(12) United States Patent
Gohla et al.

(10) Patent No.: US 9,610,463 B2
(45) Date of Patent: Apr. 4, 2017

(54) COSMETIC OR DERMATOLOGICAL PREPARATION COMPRISING COLLAGEN, CHITOSAN, GLYCOSYLAMINOGLYCAN AND CELL GROWTH PROMOTING PEPTIDE AND/OR CELLULAR COMPLEX

(75) Inventors: Sven Gohla, Oetwill am See (CH); Daniel Stangl, Meggen (CH)

(73) Assignee: BEIERSDORF AG, Hamburg (DE)

( * ) Notice: Subject to any disclaimer, the term of this patent is extended or adjusted under 35 U.S.C. 154(b) by 180 days.

(21) Appl. No.: 13/145,285

(22) PCT Filed: Feb. 1, 2010

(86) PCT No.: PCT/IB2010/000736
§ 371 (c)(1),
(2), (4) Date: Nov. 10, 2011

(87) PCT Pub. No.: WO2010/086754
PCT Pub. Date: Aug. 5, 2010

(65) Prior Publication Data
US 2012/0064182 A1    Mar. 15, 2012

Related U.S. Application Data

(60) Provisional application No. 61/148,711, filed on Jan. 30, 2009.

(51) Int. Cl.
| | | |
|---|---|---|
| A61K 36/258 | (2006.01) | |
| A61K 38/00 | (2006.01) | |
| A61K 38/04 | (2006.01) | |
| A61Q 19/08 | (2006.01) | |
| A61K 8/64 | (2006.01) | |
| A61K 8/65 | (2006.01) | |
| A61K 8/73 | (2006.01) | |
| A61K 8/97 | (2017.01) | |

(52) U.S. Cl.
CPC ............ *A61Q 19/08* (2013.01); *A61K 8/64* (2013.01); *A61K 8/65* (2013.01); *A61K 8/735* (2013.01); *A61K 8/736* (2013.01); *A61K 8/97* (2013.01)

(58) Field of Classification Search
None
See application file for complete search history.

(56) References Cited

U.S. PATENT DOCUMENTS

| | | | |
|---|---|---|---|
| 5,116,824 A | 5/1992 | Miyata et al. | |
| 5,166,187 A | 11/1992 | Collombel et al. | |
| 5,840,309 A * | 11/1998 | Herstein et al. | 424/728 |
| 6,238,888 B1 | 5/2001 | Gentz et al. | |
| 6,335,002 B1 | 1/2002 | Kogoi et al. | |
| 6,541,018 B1 | 4/2003 | Simonnet et al. | |
| 6,541,023 B1 | 4/2003 | Andre et al. | |
| 6,642,201 B1 * | 11/2003 | Khavinson et al. | 514/9.4 |
| 6,653,284 B2 | 11/2003 | Gentz et al. | |
| 6,902,737 B2 | 6/2005 | Quemin | |
| 7,939,495 B2 | 5/2011 | Chung et al. | |
| 8,507,276 B2 | 8/2013 | Gohla et al. | |
| 8,518,422 B2 | 8/2013 | Monks et al. | |
| 2002/0016295 A1 | 2/2002 | Gentz et al. | |
| 2004/0063639 A1 | 4/2004 | Gentz et al. | |
| 2004/0076598 A1 | 4/2004 | Simonnet et al. | |
| 2004/0249691 A1 * | 12/2004 | Schell et al. | 705/8 |
| 2005/0249661 A1 | 11/2005 | Higuchi et al. | |
| 2005/0249691 A1 * | 11/2005 | Monks et al. | 424/70.13 |
| 2005/0287182 A1 | 12/2005 | Monks et al. | |
| 2006/0182701 A1 | 8/2006 | Gohla et al. | |
| 2007/0237731 A1 | 10/2007 | De Oliveira Praes et al. | |
| 2007/0248675 A1 * | 10/2007 | Tae et al. | 424/486 |
| 2009/0208541 A1 | 8/2009 | Gesztesi et al. | |
| 2010/0119560 A1 | 5/2010 | Kim et al. | |
| 2012/0179069 A1 * | 7/2012 | Amirouche | 600/587 |

FOREIGN PATENT DOCUMENTS

| | | |
|---|---|---|
| DE | 4233289 A1 | 4/1994 |
| DE | 4308347 A1 | 9/1994 |
| DE | 4308445 A1 | 9/1994 |
| DE | 10128685 A1 | 12/2002 |
| EP | 0296078 A1 | 12/1988 |
| EP | 0462426 | 12/1991 |
| JP | 2001526239 A | 12/2001 |
| JP | 2007500196 A | 1/2007 |
| WO | 95/05857 | 3/1995 |
| WO | 2007/049904 A1 | 5/2007 |
| WO | WO 2007072481 A2 * | 6/2007 |

OTHER PUBLICATIONS

US 5,808,050, 09/1998, Mares-Guia (withdrawn)
"Hydrogenated Soybean Oil". From: INCI Directory. Web Updated date: Jul. 1, 2008 [Retrieved from the Internet on: Sep. 14, 2013]. Retrieved from: <URL: http://www.specialchem4cosmetics.com/services/inci/ingredient.aspx?id=5825>.*
INCI Directory. "Hydrogenated Soybean Oil". Updated: Jul. 1, 2008 [Retrieved from the Internet on: Sep. 14, 2013]. Retrieved from: <URL: http://www.specialchem4cosmetics.com/services/inci/ingredient.aspx?id=5825>.*
Fife et al. Evidence That a 550,000-Dalton Cartilage Matrix Glycoprotein Is a Chondrocyte Memrange-Associated Protein Closely Related to Ceruoplasmin; The Journal of Biological Chemistry, vol. 268, No. 6 (1993), pp. 4407-4411.*
Fugh-Berman, The 5-Minute Herb & Dietary Supplement Consult; 2003, Lippincott Williams and Wilkins, Philadelphia, Pa, p. 196.*
Great Vista Chemicals, Online, URLhttp://www.greatvistachemicals.com/biochemicals/chitin.html accessed Oct. 17, 2014, 3 pages.*
Henrotin et al. Effects of Three Avocado/Soybean Unsaponifiable Mixtures on Metal-Loproteinases, Cytokines and Prostaglandin E2 Product by Human Articular Chondrocytes; Clin Rheumatol (1998) 17:31-39.*

(Continued)

*Primary Examiner* — Chris R Tate
(74) *Attorney, Agent, or Firm* — Abel Law Group, LLP

(57) ABSTRACT

Disclosed is a cosmetic or dermatological preparation that is obtainable by combining collagen and/or a derivative thereof, chitosan and/or a derivative thereof, glycosylaminoglycan and/or a derivative thereof with a peptide that is capable of promoting skin cell growth and/or with a composition which comprises glycoproteins 1 and 2 and ginseng and horsetail extracts.

18 Claims, 21 Drawing Sheets

(56) References Cited

OTHER PUBLICATIONS

Lee et al. Effects of the Controlled-Released TGF-β1 From Chitosan Microspheres on Chondrocytes Cultured in a Collagen/Chitosan/Glycosaminoglycan Scaffold; Biomaterials 25 (2004) 4163-4173.*

Nutrition Research Center (NRC); Horsetail: An Herbal Remedy With Tradition for Healing Bones & Cartilage; Online, URL< http://nutritionresearchcenter.org/healthnews/horsetail-an-herbal-remedy-with-tradition-for-healing-bones-cartilage/> Jul. 2007, one page.*

Stanford University, Online, URL<http://cmgm.stanford.edu/biochem200/membrane_syl.html> accessed Oct. 17, 2014, 3 pages, see p. 1.*

Sung et al. Effect of Ginseng Saponon on Human Chondrocyte; J. Korea Orthop Assoc. Dec. 1998 33(7), pp. 1921-1927 (one page English Abstract provided).*

Caregen Co., Ltd: "Cosmeceutical with Growth Factors and their mimicking Peptides", Jan. 2008 (Jan. 2008), XP002669556, retrieved from the internet: URL:http://www.consultdrminas.com/data/pdf/CAREGEN_Catalogue.pdf p. 9-19.

* cited by examiner

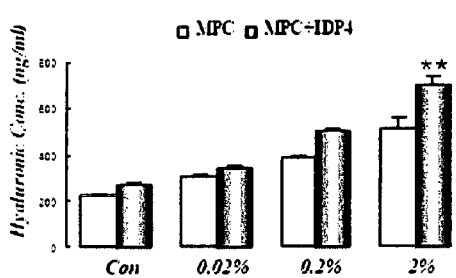
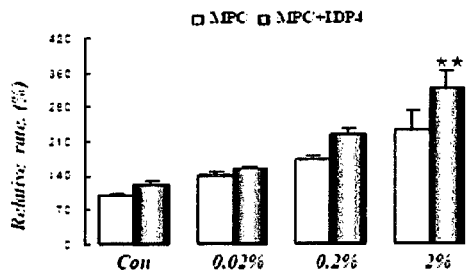
**Statistically significant peak expression ($P < 0.01$)
FIG. 7a  FIG. 7b
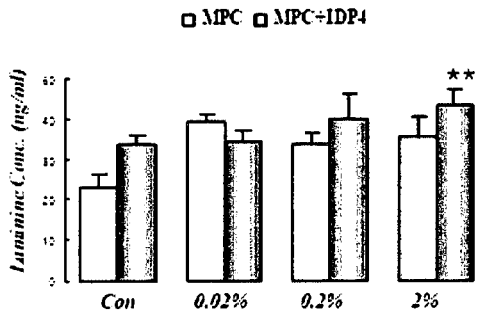
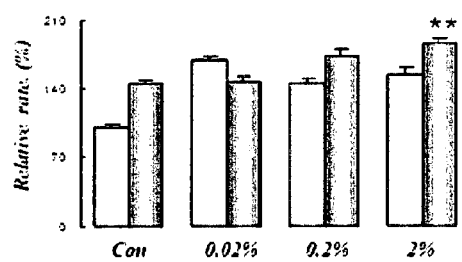
** Statistically significant peak expression ($P < 0.01$)
FIG. 8a  FIG. 8b

** Statistically significant peak expression ( p<0.01 )

GPVE+MPC, GPVE + MPC + IDP4
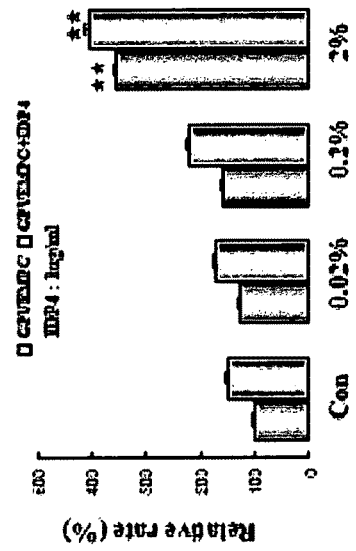
*HacaT – keratinocyte cell line*
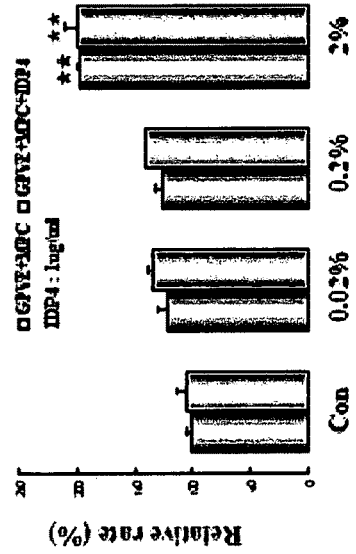
*MSC – mesenchymal stem cells*
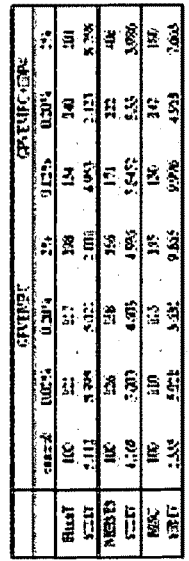
*NIH3T3 – fibroblast cell line*
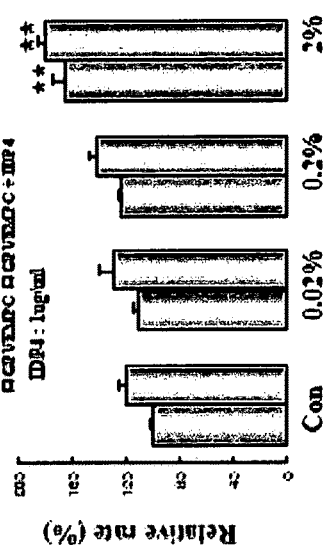
**Statistically significant peak expression ($P < 0.01$)
Cell proliferation occurred the most when added 2% and showed additive effect when used with IDP-4
FIG. 11

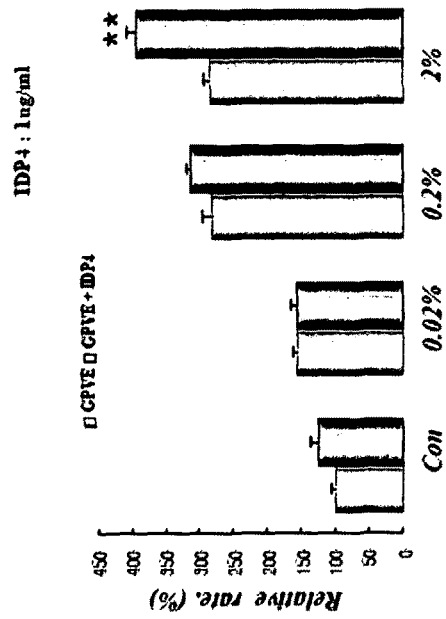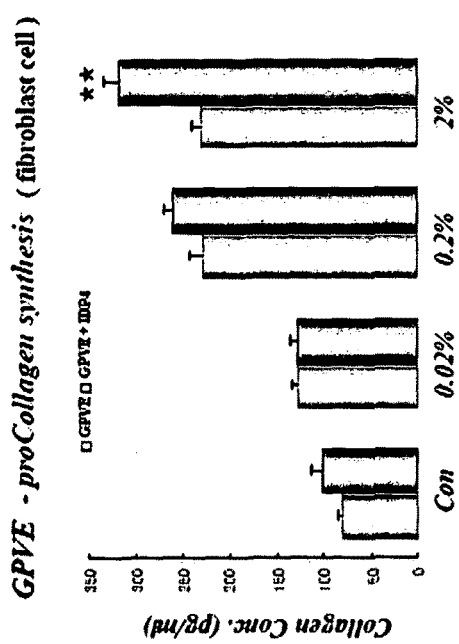
FIG. 15

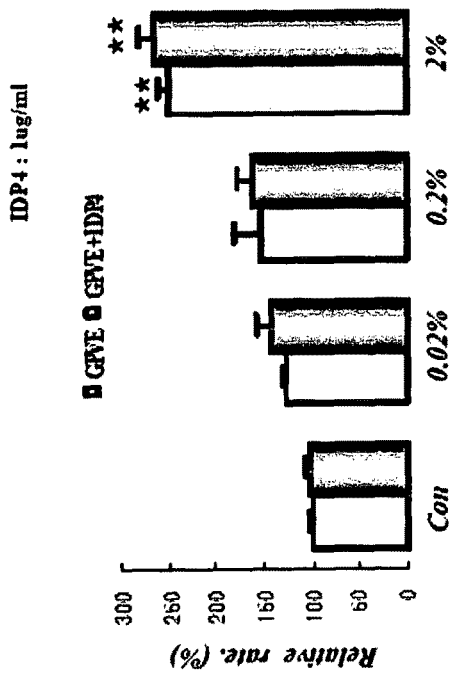
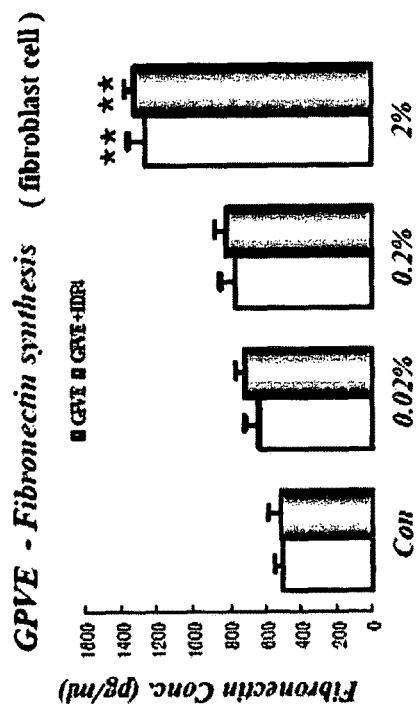
FIG. 16

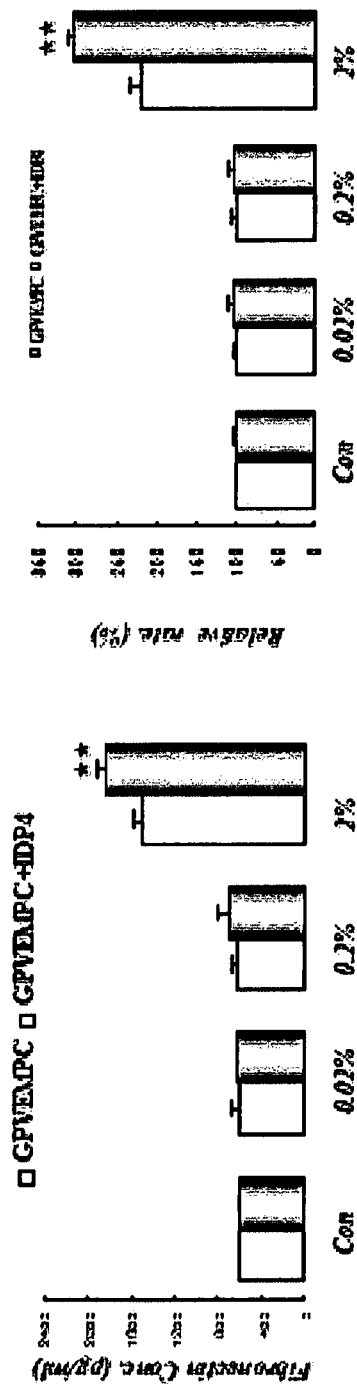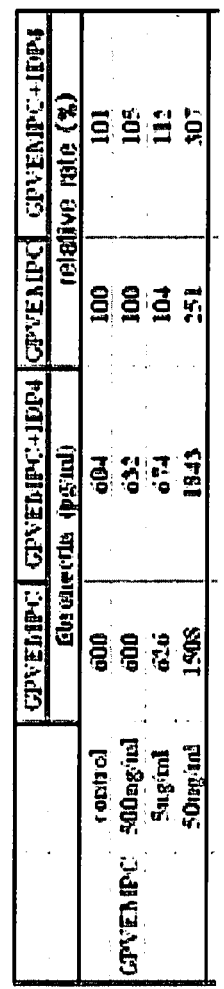
FIG. 22

COSMETIC OR DERMATOLOGICAL PREPARATION COMPRISING COLLAGEN, CHITOSAN, GLYCOSYLAMINOGLYCAN AND CELL GROWTH PROMOTING PEPTIDE AND/OR CELLULAR COMPLEX

CROSS-REFERENCE TO RELATED APPLICATIONS

The present application is a National Stage of International Application PCT/IB2010/000736, filed Feb. 1, 2010, which claims the benefit under 35 U.S.C. 119(e) of U.S. Provisional Application No. 61/148,711, filed Jan. 30, 2009, the entire disclosure whereof is incorporated by reference herein.

BACKGROUND OF THE INVENTION

1. Field of the Invention

The present invention relates to a cosmetic or dermatological preparation which is obtainable by combining collagen and/or a derivative thereof, chitosan and/or a derivative thereof and glycosylaminoglycan and/or a derivative thereof with at least one peptide which is capable of promoting skin cell growth and/or a cellular complex. In one aspect, the preparation may further comprise at least one nutrient medium phase for skin cells or corneal cells.

2. Discussion of Background Information

Various circulations exist within the human body, such as the blood circulation, the lymphatic system and the intracellular and extracellular tissue fluids. The composition of the solvent "water" with its mineral and bioorganic constituents in these various "transport media" is approximately the same and is based, highly simplified, on salts, amino acids, vitamins, sugars, proteins and proteids, and trace elements. During evolution, our body has learnt to create within these fluids "communication networks" and nutritional strategies, and an equilibrium of catabolic to anabolic processes, which make the complex life of our multicellular body possible. In this environment, our body has learnt to construct from its "single individuals", the cells, a complicated but efficient network of direct and mediator-related contacts. These "communication pathways" function efficiently and harmlessly only if the natural dynamic equilibrium of our body, the so-called "homeostasis", is maintained. If cells are removed from the tissue assemblage or if the homeostasis in the tissue assemblage is impaired, it is no longer possible for individual cells to exist or for tissues to function healthily. The medical and biosciences have for decades looked for possibilities of cultivating tissues or individual cells in suitable environmental conditions outside the body. This was successful only when it was possible to simulate as perfectly as possible the living conditions in the body for the single cells or tissue constituents to be cultivated.

Thus, if cells are removed from intact tissue, they must be cultivated in environments which come as close as possible to the natural living conditions in the body. Requirements for this are supply and transport away of nutrients, and the presence of vital factors.

These environments are well-defined compositions of mineral and biomaterials which are known in science as cell culture media. Cell culture media are obtainable from suitable specialist retailers as powder or liquid media and have slightly different compositions depending on the nature of the cells or tissue constituents to be cultivated. Cell culture media are used in liquid form. With a suitable composition, they make it possible to maintain or even multiply microorganisms or cells in culture, i.e., outside the body.

In the course of tissue research it has been possible to identify and investigate the individual needs of cells and cells in intact tissues. In this connection, the ratio of mineral and bioorganic substances of a cell culture medium is slightly variable from cell type to cell type and must be ascertained accurately for optimized survival and growth. The composition of the cell culture medium always depends on the requirements of the cells to be grown. A distinction is made between synthetic media, whose ingredients are accurately known on the basis of pure substances, and complex media, whose exact composition may vary and is in part not accurately known. Cell culture media usually comprise, besides water, a carbon source and a nitrogen source, phosphate compounds and sulfur compounds, and minerals and, optionally, growth promoters and/or vitamins.

If the compositions of the media are suitable, the cells are able to multiply and produce the factors necessary for survival "in situ" by themselves.

In order to generate good growth of the cells, serum is frequently added to the cell culture media. The serum has a complicated composition and provides the cells with, inter alia, hormones, adhesion factors, and amino acids. Culture media which contain serum are, however, costly and do not allow thermal sterilization. One therefore usually tries to make do with media which contain no serum. Serum-free culture media make it possible to cultivate cells under controlled and defined conditions, so that unwanted effects due to variations in the serum composition are eliminated. In addition, contamination of the cell cultures with viruses and bacteria is reduced when using serum-free media.

It is known that skin cells can be kept alive particularly well-preserved and for long periods of time and can even be induced to grow and differentiate in one-, two- and three-dimensional cultures by optimizing the ingredients in the culture medium. It has also been possible to demonstrate that suitable media also make possible the production of growth factors in situ.

When there are extreme changes in the skin resulting from extensive burns or chills, the integrity and the functionality of the cutaneous tissue may be so impaired that the skin is no longer able to regenerate on its own. The body responds to such severe events with hyperthermia, massive release of mediators of inflammation and irritation, and with an enormous loss of fluid, which in the past has always and inevitably resulted in the death of people with severe burns. Burns and chills which have led to losses of cutaneous tissue can be compensated by skin transplants and thus the skin can be closed. However, this is successful only if sufficient remaining skin is available for transplantation. In cases of burns of more than 60% of the total cutaneous tissue, transplantation on its own is usually of no assistance. It is necessary to re-produce viable tissue from the remaining skin cells. In this connection, because of the rejection reactions between non-HLA-compatible tissues, it is not possible to take allogeneic skin or allogeneic skin cells. It is therefore necessary to form a new cutaneous tissue in situ from the remaining viable skin cells.

The hornified epidermis forms the protective shield of the skin. For this function to be optimally exercised it is necessary for the skin cells (keratinocytes) to pass through the process of so-called epidermal differentiation. After division of the cells in the basal layer, the keratinocytes migrate to the skin surface and undergo a number of changes during this, until they form the horny layer (stratum corneum) as dead, flat, anuclear corneocytes, and eventually are desquamated. During the epidermal differentiation there is formation of various proteins having specific functions. These include, inter alfa, keratins, involucrin, filaggrin and transglutaminase. For optimal formation of the epidermis and the horny layer it is necessary for these proteins to be formed in coordinated fashion and in sufficient quantity.

Many cosmetics, skin care products or wound healing products which help to compensate or at least reduce the disorders of the skin are known in the prior art.

Thus, for example, geroderma is cosmetically treated primarily with vitamin A derivatives or hydroxy acids which lead, via stimulation of the proliferation of the basal cells in the epidermis, to a thickening of the epidermis and thus smoothing of the skin. More recent approaches consist of targeted replacement of the proteins which are absent or present in reduced quantity in dry skin or geroderma, or indirect intervention in the metabolic processes which are disturbed in dry skin or with increasing age, in order to normalize them. An example which may be mentioned here is stimulation of collagen synthesis with the aim of reducing wrinkles. In addition, for example, laminin, substances for prolonging the lifetime of skin cells and certain extracts for stimulating epidermal differentiation are employed. However, some of these are pharmacologically active substances with a high potential for side effects.

None of the preparations known from the prior art on their own enable the skin to reconstitute/regenerate itself without displaying unwanted side effects.

It would be advantageous to have available a preparation which enables the skin to regenerate itself without displaying unwanted side effects.

EP 296078, EP 462426, U.S. Pat. Nos. 5,116,824, 6,541,023 and 5,808,050 and U.S. Published Patent Application Nos. 2005/0249661 A1, 2005/0287182 A1 and 2006/0182701 A1, the entire disclosures whereof are incorporated by reference herein, disclose preparations which comprise chitosans, collagens and glycosylaminoglycans. It has now unexpectedly been found that corresponding preparations can be greatly improved by incorporating therein a peptide which is capable of promoting cell growth (or at least the part thereof which is capable of binding to skin cell receptors) and/or a composition which stimulates fibriblasts and/or keratinocytes and comprises certain glycoproteins and plant extracts. This is the first time that curing skin factors which make possible the regeneration of burnt skin ex vivo are combined with peptides and/or glycoproteins, resulting in not only a protection and distinct differentiation of skin cell clones but also in an activation of transient amplifying cells and stem cells of the dermis and epidermis (meenchymal stem cells), which has not been observed so far.

SUMMARY OF THE INVENTION

The present invention provides a cosmetic or dermatological preparation which is obtainable by combining certain substances. These substances comprise
(a) collagen and/or a derivative thereof;
(b) chitosan and/or acetylated chitosan with a degree of acetylation of up to about 50%;
(c) at least one glycosylaminoglycan and/or a derivative thereof;
and at least one (and preferably both) of (d) and (e):
(d) at last one peptide which is capable of promoting cell growth;
(e) a composition comprising
  (i) glycoprotein 1;
  (ii) glycoprotein 2;
  (iii) ginseng extract; and
  (iv) horsetail extract.

In one aspect of this preparation, at least one of the substances (a) and (b) may be of marine origin or of synthetic origin.

In another aspect, the collagen (a) may comprise one or more collagens selected from types 1, 3, 4 and 5 and/or the chitosan (b) may comprise chitosan having a molecular weight of from about 80,000 g/mol to about 15,000,000 g/mol and/or chitosan obtained from crustaceans and/or insects and/or the glycosylaminoglycan (c) may comprise chondroitin 4-sulfate and/or chondroitin 6-sulfate.

In yet another aspect, peptide (d), if present, may comprise at least one cell growth factor mimicking peptide. For example, peptide (d) may comprise oligopeptide-21 or at least a part thereof (in particular, at least that part which is capable of binding to skin cell receptors).

In a still further aspect, peptide (d), if employed, may be present in a form which substantially prevents it from contacting (a), (b) and (c) (and (e), if present) directly. For example, (d) may be present in the form of a nanoemulsion.

In another aspect, the weight ratio of (i) to the sum of (ii), (iii) and (iv) in (B) may be from about 10:90 to about 50:50, e.g., from about 20:80 to about 40:60. For example, it may be about 25:75. In yet another aspect, (e) may comprise (i), (ii), (iii) and (iv) in a total amount of from about 0.3 to about 1.2% by weight, based on the total weight of (e).

In another aspect, substances (a) to (c) may be employed in a total amount of from about 0.0005% to about 50% by weight, based on the total weight of the preparation, e.g., in a total amount of from about 0.0015% to about 30% by weight, from about 0.005% to about 10% by weight, from about 0.01% to about 1% by weight, or from about 0.015% to about 0.1% by weight.

In another aspect, peptide (d), if present, may be employed in an amount of from about 0.0001% by weight to about 1% by weight, based on the total weight of the preparation, e.g., in an amount of at least about 0.0003% by weight.

In another aspect, composition (e), if present, may be employed in an amount of from about 0.0001% by weight to about 1% by weight, based on the total weight of the preparation, e.g., in an amount of at least about 0.0003% by weight.

In another aspect of the preparation of the present invention, the weight ratio of substances (a) and (c) may be from about 35:1 to about 3:1, e.g., from about 20:1 to about 6:1, or from about 10:1 to about 8:1, and/or the weight ratio of substances (a) and (b) may be from about 10:1 to about 1.5:1, e.g., from about 7:1 to about 2.5:1, or from about 5:1 to about 3.5:1, and/or the weight ratio of the substances (b) and (c) may be from about 10:1 to about 1:1, e.g., from about 5:1 to about 1.5:1, or from about 3:1 to about 2:1.

In another aspect, the preparation of the present invention may further comprise at last one substance selected from amino acids, α-biotin, $(NH_4)_6Mo_7O_{24}$, adenine, $AlCl_3$, biotin, $CaCl_2$, calcium pantothenate, choline chloride, $CoCl_2$, $CrK(SO_4)_2$, $CuSO_4$, D-Ca pantothenate, $EDTA.Na_2$, $EDTA.Na_3$, $Fe(NO_3)_3$, $FeSO_4$, folic acid, glucose, $H_2SeO_3$, HEPES, hypoxanthine, insulin human, KCl, linoleic acid, lipoic acid, $MgCl_2$, $MnCl_2$, $MnSO_4$, myo-inositol, $Na_2HPO_4$, $Na_2SeO_3$, $Na_2SiO_3$, NaCl, $NaH_2PO_4$, $NaHCO_3$, sodium pyruvate, sodium acetate, $NH_4VO_3$, $NiCl_2$, nicotinamide, phenol red, polysorbate 80, putrescine, putrescine 2HCl, pyridoxine HCl, pyridoxal HCl, riboflavin, $SnCl_2$, thiamine HCl, thymidine, vitamin $B_{12}$, a ceramide, and $ZnSO_4$. For example, one or more of L-alanine, L-arginine, L-asparagine, L-aspartic acid, L-cysteine, L-cystine, glycine, L-glutamine, L-glutamic acid, L-histidine, L-isoleucine, L-leucine, L-lysine, L-methionine, L-phenylalanine, L-proline, L-serine, L-threonine, L-tryptophan, L-tyrosine, and L-valine may be present. In this regard, whenever in the present specification and the appended claims reference is made to an amino acid, this reference also includes the hydrochlorids salt of the amino acid. For example, "L-lysine" is intended to mean "L-lysine and/or L-lysine HCl".

In a still further aspect, the preparation of the present invention may further comprise one or more skin cell culture media. For example, the skin cell culture media may comprise DMEM/HAM F12 (1:1) and/or MCDB 153.

In yet another aspect, the preparation may comprise a nanosponge matrix and/or a microsponge matrix formed by substances (a) to (c), which matrix has been reconstituted in cell culture media. By way of non-limiting example, the cell culture media may be selected from physiological saline solution, nutrient media and complete media for culturing primary body cells, e.g., culture media for primary fibroblasts and keratinocytes. The complete media may, for example, be supplemented with serum substitutes.

In yet another aspect, the preparation of the present invention may further comprise one or more of a citrate buffer, Q10, alpha-glucosyl rutin, Zn orotate, carnitine, creatine and taurine and/or one or more alpha-hydroxy acids.

In a still further aspect, the preparation may further comprise water, for example, at least about 30% by weight of water, based on the total weight of the preparation, e.g., at least about 40%, at least about 50%, at least about 60%, at least about 70%, at least about 80%, at least about 90%, or at least about 95% by weight of water.

The present invention also provides a cosmetic or dermatological product which is selected from an aqueous gel, an O/W emulsion, a W/O/W emulsion, a W/O emulsion, a microemulsion and a cosmetic stick and which comprises the preparation of the present invention as set forth above (including the various aspects thereof).

The present invention further provides a cosmetic or dermatological product which is selected from an aqueous surfactant preparation, an emulsion, an ointment, a cream, a gel, a dusting powder, a mask, a matrix bandage, a gel bandage, a foam preparation and an aerosol preparation and comprises the preparation of the present invention as set forth above (including the various aspects thereof).

The present invention also provides an article which is selected from a wound covering, a skin covering, a patch, a pad, a tissue and a bandage and comprises the preparation of the present invention as set forth above (including the various aspects thereof).

The present invention further provides a polyurethane matrix which comprises the preparation of the present invention as set forth above (including the various aspects thereof).

The present invention also provides a cosmetic or dermatological preparation which is obtainable by combining various substances, which substances comprise
(a) collagen and/or a derivative thereof;
(b) chitosan and/or acetylated chitosan with a degree of acetylation of up to 50%;
(c) at least one glycosylaminoglycan and/or a derivative thereof; and
(d) oligopeptide-21 or at least a part thereof which is capable of binding to skin cell receptors; and/or
(e) a composition comprising
   (i) glycoprotein 1;
   (ii) glycoprotein 2;
   (iii) ginseng extract; and
   (iv) horsetail extract; as well as
(f) at least 40% by weight of water, based on the total weight of the preparation.

In this preparation, substances (a) to (c) are employed in a total amount of from about 0.005% to 10% by weight, (d), if present, is employed in an amount of from about 0.0001% to about 1% by weight, and (e), if present, is employed in an amount of from about 0.0001% to about 1% by weight, each based on the total weight of the preparation. Substances (a) and (b) are employed in a weight ratio of from about 6:1 to about 3:1 and substances (a) and (c) are employed in a weight ratio of from about 15:1 to about 7:1.

In one aspect, the preparation may further comprise folic acid, L-lysine, L-threonine, L-arginine, L-serine, L-histidine, L-tryptophan and glycine.

In another aspect, substances (a) to (c) may be employed in a total amount of from about 0.015% to about 0.1% by weight and/or (d) may be employed in an amount of from about 0.0003% to about 0.1% by weight and/or the weight ratio of substances (a) and (c) may be from about 10:1 to about 8:1 and/or the weight ratio of substances (a) and (b) may be from about 5:1 to about 3.5:1 and/or the weight ratio of substances (b) and (c) may be from about 3:1 to about 2:1.

In yet another aspect of the preparation, one or more substances selected from α-biotin, $(NH_4)_6MO_7O_{24}$, adenine, $AlCl_3$, biotin, $CaCl_2$, calcium pantothenate, choline chloride, $CoCl_2$, $CrK(SO_4)_2$, $CuSO_4$, D-Ca pantothenate, $EDTA.Na_2$, $EDTA.Na_3$, $Fe(NO_3)_3$, $FeSO_4$, $H_2SeO_3$, HEPES, hypoxanthine, insulin human, KCl, linoleic acid, lipoic acid, $MgCl_2$, $MnCl_2$, $MnSO_4$, myo-inositol, $Na_2HPO_4$, $Na_2SeO_3$, $Na_2SiO_3$, NaCl, $NaH_2PO_4$, $NaHCO_3$, sodium pyruvate, sodium acetate, $NH_4VO_3$, $NiCl_2$, nicotinamide, phenol red, polysorbate 80, putrescine, putrescine 2HCl, pyridoxine HCl, pyridoxal HCl, riboflavin, $SnCl_2$, thiamine HCl, thymidine, vitamin $B_{12}$, $ZnSO_4$, L-alanine, L-asparagine, L-aspartic acid, L-cysteine, L-cystine, glycine, L-glutamine, L-glutamic acid, L-histidine, L-isoleucine, L-leucine, L-methionine, L-phenylalanine, L-proline, L-tyrosine and L-valine may additionally be employed therein.

In a still further aspect of the preparation, the collagen may comprise one or more collagens selected from types 1, 3, 4 and 5 and/or the chitosan may comprise chitosan having a molecular weight of from about 80,000 g/mol to about 15,000,000 g/mol and/or the glycosylaminoglycan may comprise chondroitin 4-sulfate and/or chondroitin 6-sulfate.

In yet another aspect, the preparation may further comprise one or more cell culture media.

The present invention also provides a skin care method which comprises applying to the skin a preparation of the present invention as set forth above (including the various aspects thereof).

The present invention further provides a skin treatment method which comprises applying to injured and/or diseased skin a preparation of the present invention as set forth above (including the various aspects thereof).

The present invention also provides a wound management or wound healing method which comprises applying to a wound a preparation of the present invention as set forth above (including the various aspects thereof). For example, the preparation may be comprised in a wound covering, e.g., a wound covering that comprises a polyurethane.

The present invention also provides a method of generating a complete partial skin. This method comprises applying a preparation of the present invention as set forth above (including the various aspects thereof) to the surface of a body from which skin has been removed.

The present invention further provides a method of preventing or reducing scar tissue, which method comprises applying to a wound a preparation of the present invention as set forth above (including the various aspects thereof).

The present invention also provides a process for preparing a cosmetic or dermatological preparation which comprises (i) at least one of collagen and a derivative thereof, (ii) at least one of chitosan and a derivative thereof, having a degree of acetylation of up to 50%, (iii) at least one of a glycosylaminoglycan and a derivative thereof, and (iv) at least one peptide which is capable of promoting skin cell growth. This process comprises
(a) providing a solution comprising water and (i);
(b) adding (ii) to the solution of (a) to form a mixture; and
(c) adding (iii) to the mixture of (b) to form a further mixture; and
(d) combining (iv) with one or more of the solution and mixtures according to (a) to (c).
If additionally a composition is to be present which comprises glycoproteins 1 and 2 and ginseng and horsetail extracts, this composition may be added during or after any of steps (a), (b), (c) and (d) but preferably is added no later than before (d).

In one aspect of the process, (iv) may be combined with the mixture of (c).

In another aspect, the solution of (a) may comprise one or more cell culture media.

In yet another aspect, (iv) may be employed in a form which substantially prevents it from contacting (i), (ii) and (iii) directly such as, e.g., in the form of a nanoemulsion.

In another aspect of the process of the present invention, step (d) may be carried out at a temperature which is not higher than about 40° C.

In yet another aspect, the solution of (a) may comprise one or more cell culture media and/or the glycosylaminoglycan may comprise chondroitin 4-sulfate and/or chondroitin 6-sulfate and/or the collagen may comprise one or more collagens selected from types 1, 3, 4 and 5 and/or the chitosan may comprise chitosan having a molecular weight of from about 80,000 g/mol to about 15,000,000 g/mol.

In another aspect, the process may further comprise lyophilizing the mixture of (d) to provide an aerogel. Further, the aerogel may be converted into a hydrogel by introducing the aerogel into an aqueous phase, an active ingredient phase and/or a culture media phase of the cosmetic or dermatological preparation. In another aspect, the aerogel may be processed into a polyurethane matrix.

The present invention also provides a cosmetic or dermatological preparation which comprises
(A) at least one peptide which is capable of promoting skin cell growth; and
(B) a composition comprising
   (i) glycoprotein 1;
   (ii) glycoprotein 2;
   (iii) ginseng extract; and
   (iv) horsetail extract.

In one aspect of the preparation, (A) may comprise at least one growth factor mimicking oligopeptide, for example, oligopeptide-21 or a part thereof.

In another aspect, (A) may be present in a form which substantially prevents it from contacting (B) directly. For example, (A) may be present as a nanoemulsion.

In yet another aspect, the weight ratio of (i) to the sum of (ii), (iii) and (iv) in (B) may be from about 10:90 to about 50:50, e.g., from about 20:80 to about 40:60. For example, it may be about 25:75.

In a still further aspect of the preparation, (B) may comprise (i), (ii), (iii) and (iv) in a total amount of from about 0.3 to about 1.2% by weight, based on the total weight of (B).

In another aspect, (A) may be employed in an amount of from about 0.0001% by weight to about 1% by weight, based on the total weight of the preparation. For example, (A) may be present in an amount of at least about 0.0003% by weight.

In another aspect, (i), (ii), (iii) and (iv) may be present in a total amount of from about 0.0001% by weight to about 1% by weight, based on the total weight of the preparation. For example, (i), (ii), (iii) and (iv) may be employed in a total amount of at least about 0.001% by weight.

The present invention also provides a cosmetic or dermatological product which comprises the preparation set forth above (including the various aspects thereof) and is selected from an aqueous gel, an O/W emulsion, a W/O/W emulsion, a W/O emulsion, a microemulsion and a cosmetic stick and/or is selected from an aqueous surfactant preparation, an emulsion, an ointment, a cream, a gel, a dusting powder, a mask, a matrix bandage, a gel bandage, a foam and an aerosol preparation.

The present invention also provides a skin care method. The method comprises applying to skin the preparation of the present invention as set forth above (including the various aspects thereof).

The present invention also provides a skin treatment method. The method comprises applying to injured and/or diseased skin the preparation of the present invention as set forth above (including the various aspects thereof).

BRIEF DESCRIPTION OF THE DRAWINGS

The present invention is further described in the detailed description which follows, in reference to the noted plurality of drawings by way of non-limiting examples of exemplary embodiments of the present invention, wherein:

FIGS. 1-3, 10 and 11 are graphic representations of the results obtained with keratinocytes, fibroblasts and mesenchymal stem cells in the cell growth assay described below in Example 9.

FIGS. 4a to 8b are graphic representations of the results obtained with keratinocytes and fibroblasts in the Extra Cellular Matrix (ECM) expression experiments described in Example 10 below.

FIGS. 15-19 are graphic representations of the results obtained with keratinocytes and fibroblasts in the Extra Cellular Matrix (ECM) expression experiments described in Example 12 below.

FIGS. 21-25 are graphic representations of the results obtained with keratinocytes and fibroblasts in the Extra Cellular Matrix (ECM) expression experiments described in Example 13 below.

DETAILED DESCRIPTION OF THE PRESENT INVENTION

Figure 1:
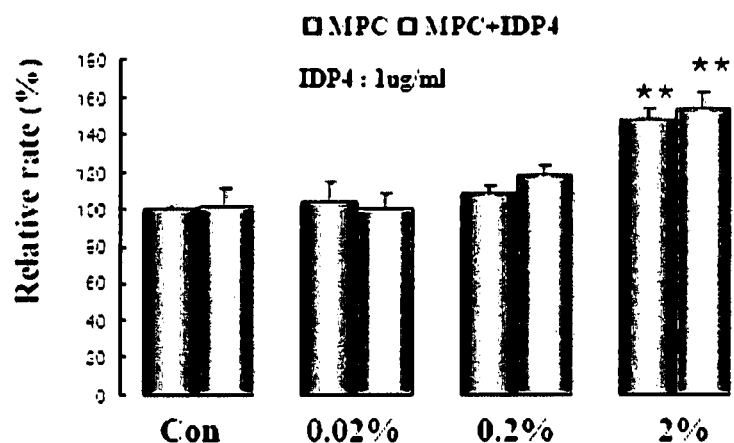
Figure 2:
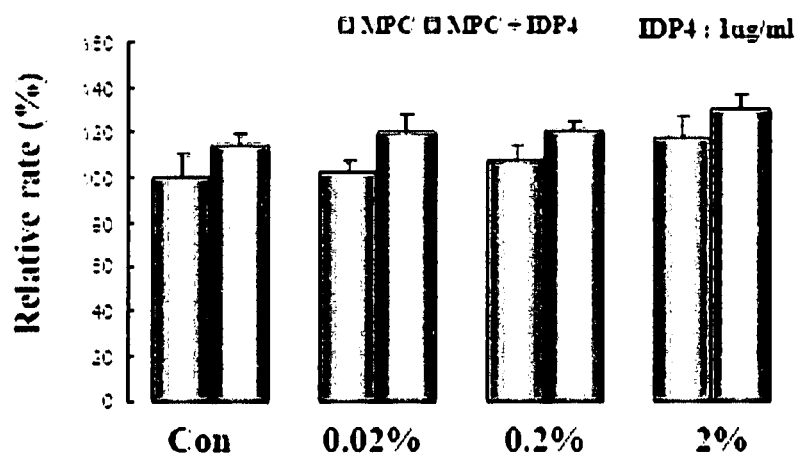

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those skilled in the art how the several forms of the present invention may be embodied in practice.

Regarding the weight ratios of the components (a) to (c) of the preparation of the present invention, it is noted that the weight ratio (a):(b) will usually be not higher than about 10:1, e.g., not higher than about 8:1, not higher than about 7:1, not higher than about 6:1, or not higher than about 5:1, and will usually be not lower than about 1.5:1, e.g., not lower than about 2:1, not lower than about 2.5:1, not lower than about 3:1, or not lower than about 3.5:1.

The weight ratio (a):(c) will usually be not higher than about 35:1, e.g., not higher than about 30:1, not higher than about 25:1, not higher than about 20:1, not higher than about 15:1, or not higher than about 10:1, and will usually be not lower than about 4:1, e.g., not lower than about 5:1, not lower than about 6:1, not lower than about 7:1, or not lower than about 8:1.

The weight ratio (b):(c) will usually be not higher than about 10:1, e.g., not higher than about 8:1, not higher than about 6:1, not higher than about 5:1, not higher than about 4:1, or not higher than about 3:1, and will usually be not lower than about 1:1, e.g., not lower than about 1.5:1, or not lower than about 2:1.

In addition to the use of glucose, folic acid, L-lysine, L-threonine, L-arginine, L-serine, L-histidine and/or glycine, the use of L-tryptophan and/or calcium pantothenate for the manufacture of the preparation of the present invention may also be of particular advantage.

The substances (a) to (c) will usually be employed in a total amount of from about 0.00001° A) by weight to about 99% by weight, based on the total weight of the preparation. However, frequently the total amount will be not higher than about 50% by weight, e.g., not higher than about 30% by weight, not higher than about 10° A) by weight, not higher than about 1° A) by weight, or not higher than about 0.1% by weight, but not lower than about 0.0001% by weight, e.g., not lower than about 0.0015% by weight, not lower than about 0.005% by weight, not lower than about 0.01% by weight, or not lower than about 0.015% by weight.

The one or more peptides (d) will usually be employed, if at all, in an amount of at least about 0.0001% by weight, e.g., at least about 0.0002%, at least about 0.0003%, or at least about 0.0004% by weight, based on the total weight of the preparation. Further, (d) will usually be employed in an amount which is not higher than about 5% by weight, e.g., not higher than about 1%, not higher than about 0.1%, not higher than about 0.01%, or not higher than about 0.001% by weight.

The peptides (d) preferably comprise at least one cell growth factor mimicking peptide. A particularly preferred example thereof is a peptide with the INCI name oligopeptide-21. This peptide is available, for example, from Caregen Co., Ltd., Korea (www.caregen.co.kr) under the trade name IDP-4. This peptide is provided in the form of a composition which in addition to 500 mg/L of oligopeptide-21 comprises 96.6% by weight of water, 1 g/L of phosphatidylcholin (lecithin), 0.1 g/L of sodium oleate, 10 ml/L of glycerol, 10 ml/L of ethanol, 2 ml/L of oil phase consisting of glycine soja (soybean) oil, 0.3722 g/L of disodium EDTA, and 10 ml/L of 2-phenoxyethanol.

In this regard, it is to be appreciated that a peptide (d) for use in the preparation of the present invention such as, e.g., oligopeptide-21, may be present in the preparation either in complete form and/or in a form which comprises at least that portion of the peptide molecule which is capable of bonding to skin cell receptors. Additionally or alternatively, the peptide may also be present in modified form, at least as long as the modification does not substantially adversely affect the ability of the peptide to serve its function. Non-limiting examples of modifications of a peptide include derivatizations of amino and/or carboxylic acid groups such as, e.g., acylation (e.g., acetylation) of one or more amino groups and esterification (e.g., with alcohols such as methanol, ethanol, propanol and isopropanol) of one or more carboxylic acid groups. Accordingly, whenever the term "peptide" is used in the present specification and the appended claims this term is intended to encompass the corresponding modified (derivatized) peptide and/or the corresponding partial peptide which comprises at least that portion of the peptide molecule which is capable of bonding to skin cell receptors and is still capable of serving the function of the (complete) peptide molecule.

Since peptides have a general tendency to associate themselves with other materials and thereby may lose at least some of their activity and/or may somewhat deactivate other components of a preparation containing them, the one or more peptides (d) are preferably employed in a form which substantially prevents their direct contact with other components of the preparation of the present invention. There are several ways to accomplish this. For example, the one or more peptides (d) may be provided in the form of colloidal systems such as, e.g., liposomal or micellar preparations or microemulsions and/or may be encapsuled/enveloped by, for example, cyclodextrins.

A currently preferred form in which the one or more peptides (d) are provided is a nanoemulsion. Nanoemulsions are emulsions of the oil-in-water type whose oil particles are enveloped by one or more emulsifiers. The oil particles are finely dispersed and the average size of the oil droplets is in the nanometer range. Often the average diameter of the oil droplets is not higher than about 100 nm, e.g., from about 50 nm to about 100 nm. Also, nanoemulsions usually have a relatively narrow droplet size distribution. Nanoemulsions may be produced, for example, by passing a mixture of aqueous and oil phases one or more times through a high pressure homogenizer which is able to mechanically break the oil phase in the presence of one or more emulsifiers, dispersing it in the aqueous phase. In the present case, the one or more peptides (d) are present in the oil phase of the nanoemulsion and are thus substantially prevented from contacting the other components of the preparation of the present invention directly.

Nanoemulsions are well known and conventionally employed especially in the pharmaceutical field and often comprise phospholipids as emulsifiers and vegetable oils (such as, e.g., soybean oil) as the oil phase. For more information regarding nanoemulsions the following documents, the entire disclosures whereof are incorporated by reference herein, may, for example, be referred to: U.S. Pat.

Nos. 6,541,018, 6,902,737, 6,335,002, US 2004/0076598 A1, US 2007/0237731 A1, WO 2006/045170, WO 2006/028339 and WO 02/80864.

(Optional) component (e) of the cosmetic and/or dermatological preparation is described, for example, in U.S. Pat. No. 5,840,309, the entire disclosure whereof is expressly incorporated herein by reference. In particular, (e) is a composition which comprises (i) glycoprotein 1, (ii) glycoprotein 2, (iii) ginseng extract, and (iv) horsetail extract. Advantageously (e) comprises, based on 100 parts by weight of (e), from about 5 to about 40, preferably about 20, parts by weight of (i), from about 25 to about 80, preferably about 50, parts by weight of (ii), from about 1 to about 10, preferably about 5, parts by weight of (iii), and from about 1 to about 10, preferably about 5, parts by weight of (iv). Advantageously the weight ratio (i)+(ii):(iii)+(iv) ranges from about 1:2 to about 1:4, and preferably is about 1:3. The weight ratio (iii):(iv) preferably is from about 3:1 to about 1:3, preferably from about 2:1 to about 1:2, and in particular about 1:1.

Composition (e) preferably comprises components (i) to (iv) in a total amount of from about 0.5 to about 50 grams per liter, preferably from about 3 to about 10 grams per liter, although higher or lower concentrations may be employed.

Component (i) of composition (e), i.e., glycoprotein 1, is commercially available (e.g., from Pentapharm, Switzerland) and comprises a purified cytoplasmatic fraction obtained from yeast and *saccharomyces*. It comprises a mixture of amino acids, nucleic acids, nucleotides, carbohydrates, lipids, oligo elements, vitamins and phosphatase enzymes.

Component (ii) of composition (e), i.e., glycoprotein 2, is also commerically available (e.g., from Sederma, France under the designation "Revitalizing GP Extract") and comprises a purified cytoplasmatic fraction obtained from *Lactobacillus*, comprising a mixture of amino acids, nucleic acids, nucleotides, carbohydrates, lipids, oligo elements, vitamins and phosphatase enzymes.

Component (iii) of composition (e) is an extract which is obtainable by extracting with a hydrophilic solvent (in particular, water, ethanol, glycol, or any mixtures thereof) the root of *Panax ginseng*. It contains saponins, sterols, carbohydrates, pectin, vitamins, minerals and lipids.

Component (iv) of composition (e) is an extract which is obtainable by extracting with a hydrophilic solvent (e.g., water, ethanol, glycol, or any mixtures thereof) the whole herb of *Equisetum arvense Linne*. It contains silicates, flavinoids, saponosides, caffeic acid and ferulic acid.

It has unexpectedly been found that a cosmetic and/or dermatological preparation which comprises a mixture that is obtainable by combining (a) collagen (and/or a collagen derivative), (b) chitosan (and/or acetylated chitosan with a degree of acetylation not exceeding about 50%) and (c) a glycosylaminoglycan (and/or a derivative thereof) with one or more peptides (d) and/or a composition (e) which comprises components (i) to (iv) set forth above is particularly effective in enabling the skin to reconstitute itself without displaying unwanted side effects to any substantial extent. For example, it has been found that oligopeptide-21 promotes the proliferation of epidermal stem cells. In combination with components (a) to (c) it provides a perfect environment and optimal conditions for the dermal and epidermal development of completely differentiated skin cells.

Preferably, preparations according to the present invention further comprise one or more skin cell culture media. DMEM/HAM F12 (1:1) and/or MCDB 153, are particularly suitable for the purposes of the present invention. In addition, all culture media which permit the culture of healthy differentiated skin (3-D models) and, in particular, media which may be used to culture primary fibroblasts and/or keratinocytes and make complete reconstitution of the skin possible are suitable as culture media for use in the present invention. Serum substitutes for serum-free cell cultures may also advantageously be used, although they are not indispensible.

A particularly advantageous combination according to the present invention comprises cell-nourishing culture media, preferably media for cultivating skin cultures or corneal cultures of all types, with a cellular matrix that comprises collagens, acetylated chitosans with a degree of acetylation of up to about 50%, preferably up to about 40%, chondroitin sulfates, and (at least) oligopeptide-21. This combination by itself, or mixed with a cosmetic preparation or incorporated into a natural or synthetic polymer matrix such as, e.g., a polyurethane matrix is extremely efficient with respect to skin regeneration/reconstitution, skin care and wound healing.

The preparation of the present invention makes it possible to regenerate skin or partial skin from individual cells (dermis and epidermis) to form a gel matrix that is precultured in vitro, to transfer this matrix to damaged tissue for complete skin renewal and/or the prevention or reduction of scar tissue associated with wound healing. The preparation of the present invention further provides the ideal environment (matrix) for renewing the skin on topical application.

A process for the preparation of a matrix that may be used in the present invention is described in, e.g., EP 296078, mentioned above.

It has been found that it is possible to obtain the matrix described in EP 296078 by using entirely marine and/or synthetic raw material sources and that the results are the same as those obtainable with the matrix of EP 296078.

In one aspect, the preparation of the present invention may be described as comprising a primary microporous or nanoporous matrix which preferably comprises marine collagens selected from the group of type 3, type 1, type 4 and/or type 5 or blends thereof, chitosans, preferably with a molecular weight of from about 80,000 D to about 15,000,000 D and with a degree of acetylation of from about 5% to about 50%, blended with a mixture of chondroitin 4- and 6-sulfates, which are preferably employed in an amount of from about 3% to about 15% by weight based on the amount of the employed collagens. The matrix can be imagined to be in the form of a microtubular or nanotubular sponge. On lyophilization, the composition of the described molecules generates a nano- or microsponge (matrix).

The matrix may be composed of an aerogel prepared by lyophilization, which matrix may be introduced into the aqueous phases, active ingredient phases and/or culture media phases of finished cosmetic or dermatological preparations. In this case, the aerogel may be converted into a hydrogel, or may be processed as aerogel, for example, together with (and/or into) a polyurethane matrix or a silicone matrix.

It has been shown that the preparation according to the present invention, especially in combination with cell culture media, results in advantages in the morphology and growth rate of primary human keratinocytes and fibroblasts from young and old donors in vitro. In principle, all growth and maintenance media are suitable for this purpose, but those which are adapted to the requirements of skin cells and enable the construction of "new skin" from individual dermis and/or epidermis cells in the described matrix usually afford the best results.

Application studies have shown that irritated skin is soothed on treatment with the matrix according to the present invention. In this regard, it is particularly advantageous if the collagen, chitosan, and glycosylaminoglycan ingredients for use in the preparation of the present invention are employed in a balanced ratio to one another, especially as described in EP 296078. In other words, formation of a micro- or nanotubular aerogel and retention of this structure in a cosmetic preparation or skin covering will usually be possible only within certain ranges of ratios of the specific active ingredients.

In this case, the stationary biopolymer phase with the disperse phase(s) composed of physiological saline solution, minimal media or complete media is converted into a hydrogel phase. The matrix components of the present invention (i.e., collagen, chitosan, glycosylaminoglycan) result in an advantageous hydrogel phase. An individual active ingredient or only two of the active ingredients alone, or the combination of active ingredients in non-advantageous proportions do not result in desirable effects, for example, a favorable interaction with the cell culture media as aqueous phase, or with polyurethane or silicone matrices.

A preferred weight ratio of the collagen and chitosan components is from about 90:10 to about 60:40, in particular from about 85:15 to about 75:25.

Collagen is a designation for a family of long-fiber, linear-colloidal, high molecular weight scleroproteins of the extracellular matrix which occur in connective tissue (e.g. skin, cartilage, tendons, ligaments, blood vessels), in osseine (the protein-containing base substance of bone) and in dentin together with proteoglycans. They are regarded as the most common animal proteins in terms of quantity, with a proportion of 25-30%. A mutual anchoring of the collagen fibers and of the cells is produced by fibronectin, which is able to bind collagen and other constituents of the extracellular matrix, but also becomes attached to receptors on cell surfaces. The composition of the collagens may vary depending on the origin. Collagens of types I to XIV are known, but only types I-III, V and XI have the described fiber structure.

When applied to the skin, advantages of the preparation of the present invention include:
Supporting the regeneration process of the skin
Providing a optimum environment for the skin
Instrumental in improving the skin structure
Soothing of skin irritations
Improving the entire condition of the skin
Improving the appearance of the skin substantially
Helping the skin to regain its elasticity and healthy impression The preparation (matrix) of the present invention may be a component of, by way of non-limiting example, aqueous gels, emulsions of the O/W, W/O/W or W/O type, microemulsions or cosmetic stick products and can thus be marketed in conventional cosmetic application forms.

In addition, the preparation of the present invention may be comprised in skin coverings, patches, pads, tissues or bandages. In this regard, polyurethane-based wound coverings are of particular interest.

An in-home-use application of the preparation of the present invention is possible, too. By way of non-limiting example, in the form of an aerogel, the matrix can be placed on the wound or the part of skin that is to be treated. The constituents of the matrix of the invention are biological polymers which can, through a specific mixing ratio, be converted into a stable aerogel and can even be reconstituted as stable hydrogel. It has been show experimentally that this gel matrix, when placed on a wound, is capable of producing complete healing skin from individual skin cells. Advantages were found and demonstrated for the preparation of the present invention for cell regeneration and proliferation of primary skin cells of the keratinocyte and fibroblast type. It is also possible through the glycosylaminoglycan, chitosan and collagen matrix interacting with the skin cells, in particular in the 3-D skin models, to induce the production of elastin, fibrillin and further biomarkers which are responsible for the quality of a healthy skin. It further is possible, through the interaction of matrix molecules, as described above, and the cell culture media, to markedly improve the reticular interlocking of the epidermis in the dermis. It is thus possible, through the preparation of the invention in interaction with the culture media, to achieve ideal regeneration of complete skin from only a few skin cells, and supply a pre-existing skin with the ideal healthy growth environment and nutrient factors. In interaction with polyurethane components, skin regeneration can be optimized under semi- or occlusive conditions, which helps to normalize in particular, keloids and other scars.

The process of producing the described matrix may advantageously comprise the addition of optionally acetylated chitosan to a collagen/water solution which may also comprise cell culture media, and the subsequent addition of a glycosylaminoglycan, preferably at least chondroitin 4-sulfate and/or chondroitin 6-sulfate. The one or more peptides (d), if employed, may be added before, during and/or after the production of the matrix, preferably in the form of a nanoemulsion. In order to not adversely affect the stability of the one or more peptides, the addition thereof is preferably carried out at a temperature of not higher than about 40° C., e.g., not higher than about 30° C. Composition (e), if employed, may be added before, during and/or after the production of the matrix, preferably before the addition of the peptide (d), if employed.

The preferred proportions of the active ingredients of the preparation according to the present invention allow sustained or controlled release of active agents such as, e.g., Q10, retinol, AHA (alpha-hydroxy acids), etc. and, in addition, may reduce or eliminate the side effects of these agents.

The most important alpha-hydroxy acids include glycolic acid, lactic acid, citric acid, tartaric acid, malic acid and salicylic acid. These acids contribute to an ablation of keratinized furfur. The skin immediately becomes smoother, fresher and softer. Pigmental moles become lighter.

Coenzyme Q10 or ubiquinone is present in almost all organisms and plays an important role in cell metabolism. Q10 also is an effective antioxidant, scavenges free radicals and stabilizes cell membranes. Thereby Q10 keeps the cells intact, functional and alive.

The term "skin cell culture medium" is intended to encompass all liquid, powdered or solid media in or on which individual cells can multiply or be cultivated. Those of skill in the art distinguish between purifying media such as, e.g., phosphate-buffered saline solution, minimal maintenance media and so-called complete media, in which cells are healthy and metabolically active. Complete media may be provided with growth factors from animal serum or so-called synthetic serum substitutes in order to improve the growth of specific cells or make same possible at all. For every cell type, but especially the culture of primary cells, there are media and media blends which support the growth, differentiation or metabolism of specific cells particularly well.

The combination of collagens, chitosans, glycosylaminoglycans (e.g., chondroitin sulfates) and peptide(s) of the present invention may be blended with all purifying, minimal or complete media, but particularly advantageously with complete media which have been composed for culturing skin cells and serve in particular as nutrient media for primary human fibroblasts and keratinocytes and which, as nutrient media, make it possible for the dermis to be regenerated from individual fibroblasts, or for the epidermis to be regenerated from individual keratinocytes. The skin cell culture media which are employed according to the present invention are thus particularly suitable for cultivating skin cells. Particular preference is given to skin cell culture media which are described as being suitable, in the composition of their individual ingredients, for the following purposes:

culture of fibroblast cells
culture of keratinocyte cells
co-cultures of keratinocytes and fibroblasts
co-cultures of fibroblasts/keratinocytes and further skin-relevant cells such as immune cells, melanocytes etc.
culture media for generating three-dimensional skin models.

The media which are preferably employed according to the present invention can act on keratinocyte/fibroblast mixed cultures and 3-D skin models.

It has surprisingly been found that cosmetic or dermatological compositions which comprise the mixture according to the present invention of biomolecules and skin cell culture media are able in or on the human skin itself to activate or simulate the mechanisms which the skin uses for homeostasis and healthy autopoiesis even better than compositions which do not comprise the one or more peptides (d). In this regard, the mixtures of fibroblast- or keratinocyte-relevant growth media may be employed directly or in suitable vesicle technologies, and may be used for medical/pharmaceutical purposes and cosmetic purposes. In particular, so-called serum-free media have proved to be advantageous when the cell fraction of the primary keratinocytes and primary fibroblasts is to be positively influenced in the sense of optimized homeostasis.

The use of the skin-relevant culture media in interaction with the matrix biomolecules brings about autologous, healthy and individual regeneration of deficient skin functions in vitro, ex vivo and in vivo. It is thus possible for regeneration of the skin, skin tautness or else simply only the contribution to skin care to be significantly improved.

In principle, all skin cell culture media are suitable for use in cosmetic preparations. Particularly suitable skin cell culture media are those employed in the literature for cultivating skin cells or skin-relevant cells, for treating skin irritations and burns. In particular, media for cultivating remaining cells after extensive burns show an extremely advantageous effect after application of the topical preparations.

Skin cell culture media which are particularly advantageous according to the present invention include media which permit neogenesis of fibroblasts or keratinocytes alone or in mixed cultures and/or which reduce the formation and passaging of non-benign cells.

The skin cell culture media DMEM/HAM F12 (1:1) and MCDB 153 are particularly suitable for use in the present invention, in particular, for use in cosmetic preparations.

According to Barnes D. and Sato G., Anal. Biochem. 102, 255 [1980], the entire disclosure whereof is incorporated by reference herein, DMEM/HAM F12 (1:1) is a 1:1 mixture where the nutrient content of HAM F12 medium is increased through addition of Dulbecco's MEM (DMEM=Dulbecco's Modified Eagles Medium). This medium is the basis for cultivating cell lines for human proteins such as, for example, erythropoetin.

DMEM/HAM F12 (1:1) medium has the following composition (in mg/L):

| | | | |
|---|---|---|---|
| NaCl | 6999.5 | L-Leucine | 59 |
| KCl | 311.8 | L-Lysine HCl | 91.25 |
| $Na_2HPO_4$ | 71 | L-Methionine | 17.24 |
| $NaH_2PO_4—H_2O$ | 62.5 | L-Phenylalanine | 35.5 |
| $MgSO_4—7H_2O$ | 100 | L-Proline | 17.25 |
| $MgCl_2—6H_2O$ | 61 | L-Serine | 26.25 |
| $CaCl_2$ | 116.61 | L-Threonine | 53.5 |
| $Fe(NO_3)_3—9H_2O$ | 0.05 | L-Tryptophan | 9 |
| $FeSO_4—7H_2O$ | 0.417 | L-Tyrosine | 38.7 |
| $CuSO_4—5H_2O$ | 0.00125 | L-Valine | 52.85 |
| $ZnSO_4—7H_2O$ | 0.432 | | |
| D-Glucose | 3151 | Choline chloride | 9 |
| $NaHCO_3$ | 2438 | α-Biotin | 0.00365 |
| Na Pyruvate | 55 | Folic acid | 2.65 |
| Phenol red | 12.5 | D-Ca pantothenate | 2.24 |
| myo-Inositol | 12.6 | | |
| L-Alanine | 4.5 | Nicotinamide | 2.02 |
| L-Arginine HCl | 147.5 | Pyridoxcal HCl | 2 |
| $L-Asparagine-H_2O$ | 7.5 | Pyridoxine HCl | 0.031 |
| L-Aspartic acid | 6.65 | Riboflavin | 0.22 |
| L-Cysteine HCl | 15.75 | Thiamine HCl | 2.17 |
| L-Cystine | 24 | Vitamin $B_{12}$ | 0.68 |
| L-Glutamine | 365.3 | Hypoxanthin | 2.05 |
| L-Glutamic acid | 7.35 | Thymidine | 0.37 |
| Glycine | 18.75 | Lipoic acid | 0.11 |
| $L-Histidine HCl—H_2O$ | 31.5 | Linoleic acid | 0.042 |
| L-Isoleucine | 54.5 | Putrescine 2HCl | 0.081 |

According to Barnes D. and Sato G., Anal. Biochem. 102, 255 [1980], MCDB 153 medium is employed for cultivating human keratinocytes. Further, as minimal medium PBS, phosphate-buffered saline, with pH values of from 3.5 to 8. MCDB 153 medium has the following composition (mg/L):

| | |
|---|---|
| NaCl | 7599 |
| Choline chloride | 13.96 |
| KCl | 111.83 |
| Putrescine | 0.1611 |
| Sodium acetate-$3H_2O$ | 500 |
| Vitamin $B_{12}$ | 4.07 |
| $Na_2HPO_4—7H_2O$ | 536.2 |
| Biotin | 0.0146 |
| $MgCl_2—6H_2O$ | 122 |
| Calcium pantothenate | 0.258 |
| $CaCl_2—2H_2O$ | 4.411 |
| Nicotinamide | 0.03663 |
| Glucose | 1081 |
| Pyridoxine HCl | 0.06171 |
| Sodium pyruvate | 55 |
| Thiamine HCl | 0.3373 |
| $NaHCO_3$ | 1176 |
| Adenine | 24.32 |
| Phenol red | 1.317 |
| myo-Inositol | 18.02 |
| HEPES | 6600 |
| Lipoic acid | 0.2063 |
| Thymidine | 0.7266 |
| L-Alanine | 8.91 |
| Folic acid | 0.79 |
| L-Arginine-HCl | 210.7 |
| Riboflavin | 0.03764 |
| L-Asparagine | 15.01 |
| L-Aspartic acid | 3.99 |
| $CuSO_4—5H_2O$ | 0.0002496 |
| $L-Cysteine HCl—H_2O$ | 42.04 |
| $FeSO_4—7H_2O$ | 1.39 |

-continued

| | |
|---|---|
| L-Glutamine | 877.2 |
| MnSO$_4$—5H$_2$O | 0.000241 |
| L-Glutamic acid | 14.71 |
| (NH$_4$)$_6$Mo$_7$O$_{24}$—4H$_2$O | 0.001236 |
| Glycine | 7.51 |
| NiCl$_2$—6H$_2$O | 0.0001188 |
| L-Histidine HCl—H$_2$O | 16.77 |
| H$_2$SeO$_3$ | 0.003869 |
| L-Isoleucine | 1.968 |
| Na$_2$SiO$_3$—9H$_2$O | 0.1421 |
| L-Leucine | 65.6 |
| SnCl$_2$—2H$_2$O | 0.0001128 |
| L-Lysine-HCl | 18.27 |
| NH$_4$VO$_3$ | 0.000585 |
| L-Methionine | 4.476 |
| ZnSO$_4$—7H$_2$O | 0.144 |
| L-Phenylalanine | 4.956 |
| L-Proline | 34.53 |
| L-Serine | 63.06 |
| L-Threonine | 11.91 |
| L-Tryptophan | 3.06 |
| L-Tyrosine | 2.718 |
| L-Valine | 35.13 |

The advantage of the DMEM/1-IAM F12 (1:1) and MCDB 153 media is that they are particularly selected and suitable in cosmetic or dermatological preparations for the cultivation of monolayer, two-dimensional and organotypical skin models, and permit the in vitro and ex vivo stimulation and/or retention of skin-specific biofunctions.

Additionally, it may be advantageous to add to the media solutions of the following compositions A and B as serum substitutes:

| Solution A | | Solution B | |
|---|---|---|---|
| Components (1000x) | μM | Components (1000x) | μM |
| FeSO$_4$—7H$_2$O | 3000 | Insulin human in 0.01M HCl | 86 |
| ZnSO$_4$—7H$_2$O | 3000 | | |
| CoCl$_2$—6H$_2$O | 1000 | | |
| CuSO$_4$—5H$_2$O | 10 | | |
| Na$_2$SeO$_3$ | 10 | | |
| AlCl$_3$—6H$_2$O | 5 | | |
| CrK(SO$_4$)$_2$—12H$_2$O | 1.4 | | |
| NiCl$_3$—6H$_2$O | 1 | | |
| MnCl$_2$—4H$_2$O | 1 | | |
| EDTA•Na$_2$—2H$_2$O | 30000 | | |
| Polysorbate 80 VG | 3820 | | |

According to the literature, the liquid media are usually prepared by using high-purity, pyrogen-free water. This water complies with the WFI quality (water for injection) of Pharmacopeia Europa. The liquid media are sterilized by filtration and bottled, the systems and methods of manufacture being such that entry of endotoxins and microbes is largely precluded.

The media that are preferred for use in the present invention show advantageous properties in relation to skin regeneration even if the media compositions are altered, such as, for example, with or without choline chloride, with or without H$_2$SeO$_3$.

The skin cell culture media and the mixture of biomolecules (collagen/chitosan/-glycosylaminoglycan/peptide(s)) and additives may advantageously be mixed into a cosmetic or dermatological preparation in a proportion of up to 99.9% by weight, based on the total weight of the preparation.

Some of the advantages associated with the preparation of the present invention which comprises a combination of certain components of cell culture media with the active ingredients collagen, chitosan and glycosylaminoglycan are illustrated in the Examples below.

In the present specification and the appended claims, cosmetic or dermatological preparations or matrices are intended to include topical preparations which are suitable for applying said media to the skin in fine distribution and preferably in a form which can be absorbed through the skin. Examples of application forms which are suitable for this purpose include aqueous and hydroalcoholic solutions, sprays, foams, foam aerosols, ointments, aqueous gels, emulsions of the O/W or W/O type, microemulsions, hydrophilic or lipophilic patches and cosmetic stick products. Particularly suitable carriers include aqueous gels, O/W emulsions, W/O/W emulsions and microemulsions. The preparation can also be used, for example, in body-cleansing compositions such as, e.g., soaps, shower baths, shampoos and the like.

Preferred cosmetic formulations include hydrogels and emulsions of any type, in particular O/W emulsions.

All lipids known for use in cosmetics can, for example, be employed as oily or lipid phase.

Preparations of the present invention in the form of an emulsion will usually comprise one or more emulsifiers. These emulsifiers may advantageously be chosen from non-ionic, anionic, cationic and amphoteric emulsifiers.

Besides water and physiologically suitable solvents, it is possible to use, inter alia, care constituents, oils, waxes, fats, refatting substances, thickeners, antioxidants, emulsifiers, substances suitable as sunscreen filters, enzymes, amino acids, proteins, polysaccharides and/or fragrances. According to the invention, apart from the aforementioned substances the preparations may optionally also comprise the additives that are customary in cosmetics, for example perfume, dyes, antimicrobial substances, refatting agents, complexing and sequestering agents, pearlescent agents, plant extracts, vitamins, active ingredients, preservatives, bactericides, coloring pigments, thickeners, emollients, moisturizers and/or humectants, and other usual ingredients of a cosmetic or dermatological formulation such as, e.g., alcohols, polyols, polymers, foam stabilizers, electrolytes, organic solvents and silicone derivatives.

Suitable preparations include also those which can be employed for professional wound management and wound healing and/or for the reduction of surgical scars and the like, such as, for example, polyurethane preparations in combination with chitosan/collagen/chondroitin 6-sulfate sponges or solutions.

Non-limiting examples of advantageous additives include specific active ingredients such as, for example, antioxidants. These antioxidants may advantageously be selected from amino acids (e.g. glycine, lysine, arginine, cysteine, cystine, histidine, tyrosine, tryptophan) and derivatives thereof (as salt, ester, ether, sugar, nucleotide, nucleoside, peptide and lipid compound), imidazoles (e.g., urocanic acid) and derivatives thereof (e.g., as salt, ester, ether, sugar, nucleotide, nucleoside, peptide and/or lipid compound), peptides such as D,L-carnosine, D-carnosine, L-carnosine, anserine and derivatives thereof (e.g., as salt, ester, ether, sugar, thiol, nucleotide, nucleoside, peptide and lipid compound), carotenoids, caro-tenes (e.g. α-carotene, β-carotene, ψ-lycopene, phytoene) and derivatives thereof (e.g., as salt, ester, ether, sugar, nucleotide, nucleoside, peptide and/or lipid compound), chlorogenic acid and derivatives thereof (e.g., as salt, ester, ether, sugar, thiol, nucleotide, nucleoside, peptide and/or lipid compound), aurothioglucose, propylthiouracil and other thiols (e.g., thioredoxin, lipoic acid, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) and the salts thereof, dilauryl thiodipropionate, distearyl thiodipropionate, thiodipropionic acid and derivatives thereof (e.g., as salt, ester, ether, sugar, thiol, nucleotide, nucleoside, peptide and/or lipid compound) and sulfoximine compounds (e.g., homocysteine sulfoximine, buthionine sulfones, penta-, hexa-, heptathionine sulfoximine) in very low tolerated dosages (e.g. pmol to μmol/kg). Also included are (metal) chelators (e.g., apoferritin, desferral, lactoferrin, α-hydroxy fatty acids, palmitic acid, phytic acid) and derivatives thereof (e.g., as salt, ester, ether, sugar, thiol, nucleotide, nucleoside, peptide and/or lipid compound), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g., γ-linolenic acid, linoleic acid, oleic acid), folic acid and derivatives thereof, furfurylidenesorbitol and derivatives thereof, ubiquinone, ubiquinol, plastoquinone and derivatives thereof (e.g., as salt, ester, ether, sugar, thiol, nucleotide, nucleoside, peptide and lipid compound), vitamin C and derivatives (e.g., ascorbyl palmitate, Mg ascorbyl phosphate, ascorbyl acetate), tocopherols and derivatives (e.g., vitamin E acetate), and phenolic compounds and plant extracts containing same such as, for example, flavonoids (e.g., glycosyl rutin, ferulic acid, caffeic acid), furfurylidene glucitol, butylated hydroxytoluene, butylated hydroxyanisole, nordihydroguaiaretic resin acid, nordi-hydroguaiaretic acid, trihydroxybutyrophenone and derivatives thereof (as salt, ester, ether, sugar, nucleotide, nucleoside, peptide and lipid compound), uric acid and derivatives thereof, mannose and derivatives thereof (e.g., as salt, ester, ether, sugar, thiol, nucleotide, nucleoside, peptide and lipid compound), zinc and its derivatives (e.g., ZnO, $ZnSO_4$), selenium and its derivatives (e.g., selenomethionine, ebselen), stilbenes and derivatives thereof (e.g., stilbene oxide, trans-stilbene oxide) and the derivatives (e.g., the salt, ester, ether, sugar, thiol, nucleotide, nucleoside, peptide and/or lipid compounds) of these active ingredients which are suitable according to the invention.

The additional use of a buffer may sometimes become necessary for stabilizing the ingredients of the disperse phase. In this regard, phosphate-buffered saline solutions and citrate buffers are examples of preferably employed buffers.

Besides antioxidants, combinations of the preparations of the present invention with specific ingredients which are preferably chosen from Q10, AGR, Zn orotate, carnitine, creatine and/or taurine are particularly preferred.

AGR (alpha-glucosyl rutin) belongs to the flavonoids which are found in most plants. AGR is capable of protecting the cells of the intrinsic immune system of the skin from environmental damage such as, e.g., from UV radiation.

Areas of application of the preparation of the present invention which have proved to be particularly advantageous include the care of all skin types with the exception of all septic inflammations, and also special applications such as microdermal abrasion, acid peeling and retinol treatments. The skin regeneration and soothing of the skin by the preparations of the present invention is evident in these cases.

An additional preferred field of application of the preparation of the present invention is cosmetic care of the skin, in particular for beautification.

The packaging for the preparation of the present invention can include all cosmetically customary dosage systems such as, e.g., jars, pump bottles, pipette bottles, cartridges or capsules.

For problematic formulations into which the cell medium cannot be incorporated, there is the possibility to mix the cell culture media and cosmetic product only shortly before use, through special packaging elements such as, for example, double cartridges with a mixing head as known, for example, from 2-component adhesives. The packaging of the cell culture medium may also be designed for refilling, so that only fresh product is used.

It also is advantageous to incorporate the matrix of the invention in a polyurethane matrix and configure the resultant product as cosmetic skin covering, wound covering in plasters or bandages or as pad. Non-limiting examples of polyurethane matrices which are suitable for these purposes include those which are described in DE 42 33 289, DE 43 08 347, DE 43 08 445, DE 43 28 190 and DE 101 28 685, the entire disclosures whereof are incorporated by reference herein.

Advantageous exemplary embodiments of the present invention follow. Unless indicated otherwise, the quantitative data are based on weight %. It is possible in all the preparations for the ratio of the matrix molecules collagen, chitosan and glycosylaminoglycan to be from about 0.00001% by weight to about 99% by weight of the final formulation, preferably from about 0.0005% by weight to about 50% by weight and ideally from about 0.0015% to about 30% by weight, based on the total weight of the preparation. The dispersant "culture medium" preferably corresponds to an osmotic pressure of an about 0.5% to about 2% sodium chloride solution, but ideally corresponds to the physiological osmotic pressure of human tissue, especially of the skin.

EXAMPLES

Example 1

Day Cream

| Formula (INCI/CTFA adopted names) | % w/w |
|---|---|
| WATER (AQUA) | 63.4277 |
| GLYCERIN | 5.3600 |
| CAPRYLIC/CAPRIC TRIGLYCERIDE | 5.0000 |
| ETHYLHEXYL METHOXYCINNAMATE | 3.0000 |
| SUCROSE DISTEARATE | 2.5000 |
| CETYL ALCOHOL | 2.5000 |
| TRIETHYLHEXANOIN | 2.0000 |
| CETEARYL ALCOHOL | 1.8000 |
| HYDROGENATED COCO-GLYCERIDES | 1.7000 |
| TRIDECYL STEARATE | 1.4700 |
| TRIDECYL TRIMELLITATE | 1.1100 |
| *MACADAMIA TERNIFOLIA* SEED OIL | 1.0000 |
| *BUTYROSPERMUM PARKII* (SHEA BUTTER) | 1.0000 |
| PHENOXYETHANOL | 0.7706 |
| PANTHENOL | 0.7500 |
| SUCROSE STEARATE | 0.7000 |
| TOCOPHERYL ACETATE | 0.6000 |
| GLYCERYL ACRYLATE/ACRYLIC ACID COPOLYMER | 0.4389 |
| DIPENTAERYTHRITYL HEXACAPRYLATE/HEXACAPRATE | 0.4200 |
| FRAGRANCE (PARFUM) | 0.4157 |
| CYCLOPENTASILOXANE | 0.3250 |
| METHYLPARABEN | 0.3171 |
| CHOLESTEROL | 0.3150 |
| SODIUM LAUROYL LACTYLATE | 0.3000 |

-continued

| Formula (INCI/CTFA adopted names) | % w/w |
|---|---|
| PROPYLENE GLYCOL | 0.3000 |
| GALACTOARABINAN | 0.3000 |
| BUTYLENE GLYCOL | 0.2659 |
| XANTHAN GUM | 0.2090 |
| PROPYLPARABEN | 0.2073 |
| ETHYLPARABEN | 0.2002 |
| CYCLOHEXASILOXANE | 0.1750 |
| TITANIUM DIOXIDE | 0.1550 |
| ACRYLATES/C10-30 ALKYL ACRYLATE CROSSPOLYMER | 0.1500 |
| CARBOMER | 0.1090 |
| DISODIUM EDTA | 0.1029 |
| ETHYLHEXYLGLYCERIN | 0.0800 |
| MICA | 0.0720 |
| YEAST (FAEX) EXTRACT | 0.0500 |
| SILICA | 0.0328 |
| SODIUM HYDROXIDE | 0.0300 |
| HYDROXYISOHEXYL 3-CYCLOHEXENE CARBOXALDEHYDE | 0.0300 |
| CERAMIDE 3 | 0.0300 |
| BUTYLPHENYL METHYLPROPIONAL | 0.0200 |
| ALUMINA | 0.0200 |
| LIMONENE | 0.0192 |
| SOLUBLE COLLAGEN | 0.0171 |
| PHYTOSPHINGOSINE | 0.0150 |
| CERAMIDE 6 II | 0.0150 |
| HEXYL CINNAMAL | 0.0100 |
| ALCOHOL | 0.0100 |
| PVM/MA COPOLYMER | 0.0090 |
| SODIUM POLYACRYLATE | 0.0075 |
| HYDROLYZED CONCHIOLIN PROTEIN | 0.0050 |
| BENZYL SALICYLATE | 0.0050 |
| CHITOSAN | 0.0046 |
| SODIUM METHYLPARABEN | 0.0040 |
| SODIUM CHLORIDE | 0.0027 |
| *GLYCINE SOJA* (SOYBEAN) OIL | 0.0020 |
| SODIUM CHONDROITIN SULFATE | 0.0019 |
| GLUCOSE | 0.0019 |
| BUTYLPARABEN | 0.0017 |
| HYDROGENATED LECITHIN | 0.0010 |
| LYSINE HCL | 0.0006 |
| OLIGOPEPTIDE-21 | 0.0005 |
| THREONINE | 0.0004 |
| ISOBUTYLPARABEN | 0.0004 |
| ARGININE | 0.0004 |
| SERINE | 0.0002 |
| POTASSIUM CHLORIDE | 0.0002 |
| HISTIDINE | 0.0002 |
| TRYPTOPHAN | 0.0001 |
| SODIUM PHOSPHATE | 0.0001 |
| SODIUM OLEATE | 0.0001 |
| MAGNESIUM SULFATE | 0.0001 |
| LINALOOL | 0.0001 |
| GLYCINE | 0.0001 |
| CALCIUM CHLORIDE | 0.0001 |
| TOCOPHEROL | 0.0001 |
| GERANIOL | 0.0001 |
| FOLIC ACID | 0.0001 |
| CITRAL | 0.0001 |
| CERAMIDE 1 | 0.0001 |
| CALCIUM PANTOTHENATE | 0.0001 |
| BENZYL ALCOHOL | 0.0001 |
| TITANIUM DIOXIDE | 0.1040 |
| | 100.0000 |

Example 2

Night Cream

| Formula (INCI/CTFA adopted names) | % w/w |
|---|---|
| WATER (AQUA) | 59.6000 |
| GLYCERIN | 5.2350 |
| MYRISTYL LACTATE | 4.0000 |

-continued

| Formula (INCI/CTFA adopted names) | % w/w |
|---|---|
| CYCLOPENTASILOXANE | 3.9950 |
| HYDROGENATED COCO-GLYCERIDES | 3.0000 |
| *BUTYROSPERMUM PARKII* (SHEA BUTTER) | 2.5000 |
| PROPYLHEPTYL CAPRYLATE | 2.0000 |
| PENTYLENE GLYCOL | 2.0000 |
| OCTYLDODECANOL | 2.0000 |
| GLYCERYL STEARATE SE | 2.0000 |
| GLYCERYL STEARATE CITRATE | 2.0000 |
| CETEARYL ALCOHOL | 2.0000 |
| CYCLOHEXASILOXANE | 1.4000 |
| *LIMNANTHES ALBA* (MEADOWFOAM) SEED OIL | 1.0000 |
| ISONONYL ISONONANOATE | 1.0000 |
| AMMONIUM ACRYLOYLDIMETHYLTAURATE/ VP COPOLYMER | 0.7600 |
| PANTHENOL | 0.7500 |
| TOCOPHERYL ACETATE | 0.6500 |
| PHENOXYETHANOL | 0.5044 |
| DIMETHICONE | 0.5000 |
| VEGETABLE (OLUS) OIL | 0.3000 |
| *NARCISSUS TAZETTA* BULB EXTRACT | 0.3000 |
| GALACTOARABINAN | 0.3000 |
| XANTHAN GUM | 0.2300 |
| SODIUM STEAROYL LACTYLATE | 0.2100 |
| METHYLPARABEN | 0.2071 |
| PROPYLPARABEN | 0.2015 |
| SODIUM LACTATE | 0.1500 |
| POLYSILICONE-11 | 0.1050 |
| ETHYLPARABEN | 0.1015 |
| ARGININE | 0.1004 |
| DISODIUM PHOSPHATE | 0.1000 |
| CITRIC ACID | 0.1000 |
| CETYL ALCOHOL | 0.0900 |
| FRAGRANCE (PARFUM) | 0.0831 |
| GLYCERYL DIBEHENATE | 0.0825 |
| ETHYLHEXYLGLYCERIN | 0.0505 |
| DISODIUM EDTA | 0.0504 |
| TRIBEHENIN | 0.0450 |
| SODIUM HYALURONATE | 0.0300 |
| BHT | 0.0300 |
| HYDROXYISOHEXYL 3-CYCLOHEXENE CARBOXALDEHYDE | 0.0286 |
| RUTIN | 0.0250 |
| SODIUM CARBOXYMETHYL BETA-GLUCAN | 0.0240 |
| GLYCERYL BEHENATE | 0.0225 |
| BUTYLENE GLYCOL | 0.0209 |
| SOLUBLE COLLAGEN | 0.0171 |
| *GLYCINE SOJA* (SOYBEAN) STEROLS | 0.0150 |
| ALPHA-ISOMETHYL IONONE | 0.0110 |
| BUTYLPHENYL METHYLPROPIONAL | 0.0102 |
| POLYSORBATE 80 | 0.0100 |
| ALCOHOL | 0.0100 |
| CITRONELLOL | 0.0062 |
| CARNOSINE | 0.0060 |
| LINALOOL | 0.0059 |
| CHITOSAN | 0.0046 |
| LIMONENE | 0.0041 |
| BUTYLPARABEN | 0.0030 |
| SODIUM CHLORIDE | 0.0027 |
| *GLYCINE SOJA* (SOYBEAN) OIL | 0.0020 |
| SODIUM CHONDROITIN SULFATE | 0.0019 |

Example 3

Nourishing Day Cream

| Formula (INCI/CTFA adopted names) | % w/w |
|---|---|
| WATER (AQUA) | 64.8125 |
| ISOPROPYL STEARATE | 5.5000 |
| HYDROGENATED POLYISOBUTENE | 5.0000 |
| STEARYL ALCOHOL | 3.6000 |

-continued

| Formula (INCI/CTFA adopted names) | % w/w |
|---|---|
| HYDROGENATED COCO-GLYCERIDES | 3.0000 |
| ACETYLATED LANOLIN | 3.0000 |
| CETYL ALCOHOL | 2.6000 |
| PETROLATUM | 1.8000 |
| HYDROGENATED COCONUT OIL | 1.5000 |
| PEG-30 STEARATE | 1.4000 |
| GLYCERYL STEARATE | 1.2000 |
| GLYCERIN | 0.9200 |
| SORBITAN SESQUIOLEATE | 0.9000 |
| PHENOXYETHANOL | 0.8992 |
| LANOLIN | 0.6000 |
| ETHYLHEXYL METHOXYCINNAMATE | 0.5000 |
| BUTYL METHOXYDIBENZOYLMETHANE | 0.5000 |
| POLOXAMER 188 | 0.3000 |
| HEXYL CINNAMAL | 0.2271 |
| RETINYL PALMITATE | 0.2178 |
| GLYCERYL ACRYLATE/ACRYLIC ACID COPOLYMER | 0.2150 |
| PPG-26 | 0.2000 |
| PANTHENOL | 0.2000 |
| METHYLPARABEN | 0.1970 |
| DISODIUM EDTA | 0.1004 |
| CARBOMER | 0.1000 |
| PROPYLPARABEN | 0.0970 |
| FRAGRANCE (PARFUM) | 0.0901 |
| LECITHIN | 0.0550 |
| ETHYLPARABEN | 0.0362 |
| LINALOOL | 0.0232 |
| BUTYLENE GLYCOL | 0.0209 |
| SODIUM HYDROXIDE | 0.0200 |

Example 4

Skin Serum

| Formula (INCI/CTFA adopted names) | % w/w |
|---|---|
| WATER (AQUA) | 87.1238 |
| PENTYLENE GLYCOL | 5.0000 |
| GLYCERIN | 3.1100 |
| SD ALCOHOL 3-C (ALCOHOL DENAT.) | 2.0000 |
| PANTHENOL | 0.9000 |
| CARBOMER | 0.3700 |
| XANTHAN GUM | 0.3000 |
| GLYCERYL ACRYLATE/ACRYLIC ACID COPOLYMER | 0.2926 |
| METHYLPARABEN | 0.2032 |
| PROPYLENE GLYCOL | 0.2000 |
| SODIUM HYDROXIDE | 0.1100 |
| DISODIUM EDTA | 0.1004 |
| SODIUM BENZOATE | 0.1000 |
| CITRIC ACID | 0.0500 |
| BIOTIN | 0.0400 |
| PHENOXYETHANOL | 0.0256 |
| BUTYLENE GLYCOL | 0.0209 |
| SOLUBLE COLLAGEN | 0.0171 |
| ALCOHOL | 0.0100 |
| PVM/MA COPOLYMER | 0.0060 |
| CHITOSAN | 0.0046 |
| SODIUM CHLORIDE | 0.0027 |
| GLYCINE SOJA (SOYBEAN) OIL | 0.0020 |
| SODIUM CHONDROITIN SULFATE | 0.0019 |
| GLUCOSE | 0.0019 |
| BUTYLPARABEN | 0.0017 |
| PROPYLPARABEN | 0.0011 |
| PHOSPHATIDYLCHOLINE | 0.0010 |
| LYSINE HCL | 0.0006 |
| OLIGOPEPTIDE-21 | 0.0005 |
| THREONINE | 0.0004 |
| ISOBUTYLPARABEN | 0.0004 |
| ARGININE | 0.0004 |
| SERINE | 0.0002 |

-continued

| Formula (INCI/CTFA adopted names) | % w/w |
|---|---|
| POTASSIUM CHLORIDE | 0.0002 |
| HISTIDINE | 0.0002 |
| ETHYLPARABEN | 0.0002 |
| TRYPTOPHAN | 0.0001 |
| SODIUM PHOSPHATE | 0.0001 |
| SODIUM OLEATE | 0.0001 |
| MAGNESIUM SULFATE | 0.0001 |
| GLYCINE | 0.0001 |
| CALCIUM CHLORIDE | 0.0001 |
| FOLIC ACID | 0.0001 |
| CALCIUM PANTOTHENATE | 0.0001 |
| | 100.0004 |

Example 5

Day Cream

| Formula (INCI/CTFA adopted names) | % w/w |
|---|---|
| WATER (AQUA) | 66.1473 |
| CYCLOPENTASILOXANE | 5.6000 |
| BUTYLENE GLYCOL | 5.0209 |
| GLYCERYL STEARATE SE | 3.5000 |
| GLYCERIN | 3.0100 |
| HYDROXYPROPYL CYCLODEXTRIN | 2.1000 |
| CYCLOHEXASILOXANE | 2.1000 |
| ISOPROPYL PALMITATE | 2.0000 |
| GLYCERYL STEARATE CITRATE | 1.5000 |
| POLY(GLYCOL ADIPATE)/BIS-HYDROXYETHOXYPROPYL DIMETHICONE COPOLYMER | 1.0000 |
| OCTYLDODECANOL | 1.0000 |
| MANGIFERA INDICA (MANGO) SEED OIL | 1.0000 |
| PHENOXYETHANOL | 0.7736 |
| PANTHENOL | 0.7500 |
| TOCOPHERYL ACETATE | 0.6000 |
| HYDROXYPROPYL STARCH PHOSPHATE | 0.6000 |
| SODIUM POLYSTYRENE SULFONATE | 0.5000 |
| METHYLPARABEN | 0.3141 |
| NYLON-12 | 0.3000 |
| DIMETHICONOL | 0.3000 |
| CARBOMER | 0.2055 |
| XANTHAN GUM | 0.2000 |
| HYDROLYZED WHEAT PROTEIN | 0.2000 |
| BENZOPHENONE-3 | 0.2000 |
| ARGANIA SPINOSA KERNEL EXTRACT | 0.1800 |
| FRAGRANCE (PARFUM) | 0.1124 |
| ARGININE | 0.1004 |
| CHONDRUS CRISPUS (CARRAGEENAN) | 0.1000 |
| PROPYLPARABEN | 0.0808 |
| PROPYLENE GLYCOL | 0.0700 |
| POLYACRYLAMIDE | 0.0525 |
| DISODIUM EDTA | 0.0504 |
| SODIUM HYALURONATE | 0.0500 |
| ETHYLPARABEN | 0.0302 |
| SODIUM COCOYL GLUTAMATE | 0.0300 |
| C13-14 ISOPARAFFIN | 0.0255 |
| HYDROXYCITRONELLAL | 0.0182 |
| SOLUBLE COLLAGEN | 0.0171 |
| BENZYL SALICYLATE | 0.0163 |
| ALPHA-ISOMETHYL IONONE | 0.0149 |
| PHOSPHOLIPIDS | 0.0130 |
| LAURETH-7 | 0.0120 |
| SODIUM METHYLPARABEN | 0.0105 |
| SODIUM DEHYDROACETATE | 0.0105 |
| BUTYLPHENYL METHYLPROPIONAL | 0.0102 |
| ALCOHOL | 0.0100 |
| TETRASODIUM EDTA | 0.0070 |
| SORBIC ACID | 0.0070 |
| LINALOOL | 0.0067 |
| BENZYL BENZOATE | 0.0049 |

| Formula (INCI/CTFA adopted names) | % w/w |
|---|---|
| CHITOSAN | 0.0046 |
| BENZYL ALCOHOL | 0.0043 |
| AMYL CINNAMAL | 0.0037 |
| SODIUM CHLORIDE | 0.0027 |
| ISOEUGENOL | 0.0025 |
| EUGENOL | 0.0025 |
| SPHINGOLIPIDS | 0.0020 |
| GLYCINE SOJA (SOYBEAN) OIL | 0.0020 |
| SODIUM CHONDROITIN SULFATE | 0.0019 |
| GLUCOSE | 0.0019 |
| BUTYLPARABEN | 0.0017 |
| PHOSPHATIDYLCHOLINE | 0.0010 |
| CITRONELLOL | 0.0009 |
| LIMONENE | 0.0008 |
| LYSINE HCL | 0.0006 |
| GERANIOL | 0.0006 |
| OLIGOPEPTIDE-21 | 0.0005 |
| HEXYL CINNAMAL | 0.0005 |
| THREONINE | 0.0004 |
| ISOBUTYLPARABEN | 0.0004 |
| BENZYL CINNAMATE | 0.0004 |
| SERINE | 0.0002 |
| POTASSIUM CHLORIDE | 0.0002 |
| HISTIDINE | 0.0002 |
| TRYPTOPHAN | 0.0001 |
| SODIUM PHOSPHATE | 0.0001 |
| SODIUM OLEATE | 0.0001 |
| MAGNESIUM SULFATE | 0.0001 |
| GLYCINE | 0.0001 |
| CITRAL | 0.0001 |
| CALCIUM CHLORIDE | 0.0001 |
| FOLIC ACID | 0.0001 |
| FARNESOL | 0.0001 |
| CALCIUM PANTOTHENATE | 0.0001 |
| ANISE ALCOHOL | 0.0001 |
| YELLOW 6 | 0.0003 |
| RED 4 | 0.0002 |
| | 100.0000 |

Example 6

Master Cream

| Formula (INCI/CTFA adopted names) | % w/w |
|---|---|
| WATER (AQUA) | 54.4039 |
| GLYCERIN | 5.3250 |
| MYRISTYL LACTATE | 5.0000 |
| CYCLOPENTASILOXANE | 3.7700 |
| *BUTYROSPERMUM PARKII* (SHEA BUTTER) | 3.0800 |
| GLYCERYL STEARATE CITRATE | 3.0000 |
| HYDROGENATED COCO-GLYCERIDES | 2.5000 |
| PENTYLENE GLYCOL | 2.2000 |
| PROPYLHEPTYL CAPRYLATE | 2.0000 |
| OCTYLDODECANOL | 2.0000 |
| CETEARYL ALCOHOL | 2.0000 |
| POLY(GLYCOLADIPATE)/BIS-HYDROXYETHOXYPROPYL DIMETHICONE COPOLYMER | 1.5000 |
| PEG-30 STEARATE | 1.1000 |
| CYCLOHEXASILOXANE | 1.0500 |
| LAUROYL LYSINE | 1.0000 |
| BUTYL METHOXYDIBENZOYLMETHANE | 1.0000 |
| AMMONIUM ACRYLOYLDIMETHYLTAURATE/VP COPOLYMER | 0.7600 |
| PANTHENOL | 0.7500 |
| GLYCERYL DIBEHENATE | 0.6600 |
| PROPYLENE GLYCOL | 0.6250 |
| TOCOPHERYL ACETATE | 0.6000 |
| PHENOXYETHANOL | 0.5261 |
| *FUMARIA OFFICINALIS* FLOWER/LEAF/STEM EXTRACT | 0.5000 |
| *CITRUS MEDICA LIMONUM* (LEMON) FRUIT EXTRACT | 0.5000 |
| TRIBEHENIN | 0.3600 |
| CAPRYLIC/CAPRIC TRIGLYCERIDE | 0.3200 |
| GALACTOARABINAN | 0.3000 |
| FRAGRANCE (PARFUM) | 0.2810 |
| BUTYLENE GLYCOL | 0.2619 |
| HYDROGENATED LECITHIN | 0.2410 |
| XANTHAN GUM | 0.2390 |
| METHYLPARABEN | 0.2021 |
| PROPYLPARABEN | 0.2008 |
| POLOXAMER 188 | 0.2000 |
| CAFFEINE | 0.2000 |
| GLYCERYL BEHENATE | 0.1800 |
| ARGININE | 0.1704 |
| FUMARIC ACID | 0.1250 |
| POLYSILICONE-11 | 0.1050 |
| ETHYLPARABEN | 0.1002 |
| DISODIUM PHOSPHATE | 0.1000 |
| DIMETHICONOL | 0.0750 |
| *HIBISCUS ABELMOSCHUS* SEED EXTRACT | 0.0700 |
| ETHYLHEXYLGLYCERIN | 0.0505 |
| DISODIUM EDTA | 0.0504 |
| LECITHIN | 0.0400 |
| CITRIC ACID | 0.0400 |
| SODIUM HYALURONATE | 0.0300 |
| BHT | 0.0300 |
| RUTIN | 0.0250 |
| BUTYLPHENYL METHYLPROPIONAL | 0.0210 |
| BENZYL SALICYLATE | 0.0210 |
| SQUALANE | 0.0200 |
| SOLUBLE COLLAGEN | 0.0171 |
| HEXYL CINNAMAL | 0.0158 |
| POLYSORBATE 80 | 0.0100 |
| ALCOHOL | 0.0100 |
| *LEPIDIUM SATIVUM* SPROUT EXTRACT | 0.0048 |
| CHITOSAN | 0.0046 |
| CERAMIDE 3 | 0.0040 |
| BENZYL ALCOHOL | 0.0035 |
| SODIUM CHLORIDE | 0.0027 |
| GERANIOL | 0.0025 |
| LINALOOL | 0.0023 |
| HYDROXYCITRONELLAL | 0.0021 |
| *GLYCINE SOJA* (SOYBEAN) OIL | 0.0020 |
| SODIUM CHONDROITIN SULFATE | 0.0019 |
| GLUCOSE | 0.0019 |
| BUTYLPARABEN | 0.0017 |
| LIMONENE | 0.0007 |
| LYSINE HCL | 0.0006 |
| OLIGOPEPTIDE-21 | 0.0005 |
| THREONINE | 0.0004 |
| ISOBUTYLPARABEN | 0.0004 |
| SERINE | 0.0002 |
| POTASSIUM CHLORIDE | 0.0002 |
| HISTIDINE | 0.0002 |
| TRYPTOPHAN | 0.0001 |
| SODIUM PHOSPHATE | 0.0001 |
| SODIUM OLEATE | 0.0001 |
| MAGNESIUM SULFATE | 0.0001 |
| ISOEUGENOL | 0.0001 |
| GLYCINE | 0.0001 |
| CALCIUM CHLORIDE | 0.0001 |
| FOLIC ACID | 0.0001 |
| CITRONELLOL | 0.0001 |
| CALCIUM PANTOTHENATE | 0.0001 |
| BENZYL BENZOATE | 0.0001 |
| AMYL CINNAMAL | 0.0001 |
| YELLOW 6 | 0.0002 |
| | 100.0008 |

Example 7

Eye Cream

| Formula (INCI/CTFA adopted names) | % w/w |
|---|---|
| WATER (AQUA) | 65.0059 |
| GLYCERIN | 4.4977 |
| POLYDECENE | 3.0000 |
| HYDROGENATED POLYISOBUTENE | 3.0000 |
| ETHYLHEXYL METHOXYCINNAMATE | 3.0000 |
| TRIISOSTEARIN | 2.5000 |
| C12-16 ALCOHOLS | 2.2800 |
| TOCOPHERYL ACETATE | 2.0000 |
| HYDROGENATED COCO-GLYCERIDES | 1.7000 |
| CETEARYL ALCOHOL | 1.5000 |
| BUTYL METHOXYDIBENZOYLMETHANE | 1.4000 |
| CYCLOPENTASILOXANE | 1.3000 |
| HYDROGENATED LECITHIN | 1.2500 |
| *BUTYROSPERMUM PARKII* (SHEA BUTTER) | 1.1000 |
| OCTYLDODECANOL | 1.0000 |
| ALUMINUM STARCH OCTENYLSUCCINATE | 0.8800 |
| PHENOXYETHANOL | 0.7506 |
| CYCLOHEXASILOXANE | 0.7000 |
| PALMITIC ACID | 0.5700 |
| GLYCERYL ACRYLATE/ACRYLIC ACID COPOLYMER | 0.4300 |
| POLYVINYL ALCOHOL | 0.4000 |
| CAPRYLIC/CAPRIC TRIGLYCERIDE | 0.4000 |
| IMIDAZOLIDINYL UREA | 0.3060 |
| PENTYLENE GLYCOL | 0.2500 |
| XANTHAN GUM | 0.2300 |
| METHYLPARABEN | 0.1531 |
| DISODIUM EDTA | 0.1000 |
| TROMETHAMINE | 0.0600 |
| BUTYLPARABEN | 0.0417 |
| ETHYLPARABEN | 0.0402 |
| SQUALANE | 0.0250 |
| PROPYLPARABEN | 0.0211 |
| BUTYLENE GLYCOL | 0.0209 |
| ISOBUTYLPARABEN | 0.0204 |
| CITRIC ACID | 0.0200 |
| SOLUBLE COLLAGEN | 0.0171 |
| PROPYLENE GLYCOL | 0.0100 |
| CERAMIDE 3 | 0.0050 |
| CHITOSAN | 0.0046 |
| SODIUM CHLORIDE | 0.0027 |
| SODIUM CHONDROITIN SULFATE | 0.0019 |
| GLUCOSE | 0.0019 |
| ALCOHOL | 0.0010 |
| LYSINE HCL | 0.0006 |
| THREONINE | 0.0004 |
| ARGININE | 0.0004 |
| SERINE | 0.0002 |
| POTASSIUM CHLORIDE | 0.0002 |
| HISTIDINE | 0.0002 |
| *GLYCINE SOJA* (SOYBEAN) OIL | 0.0002 |
| TRYPTOPHAN | 0.0001 |
| SODIUM PHOSPHATE | 0.0001 |
| PHOSPHATIDYLCHOLINE | 0.0001 |
| OLIGOPEPTIDE-21 | 0.0001 |
| MAGNESIUM SULFATE | 0.0001 |
| GLYCINE | 0.0001 |
| CALCIUM CHLORIDE | 0.0001 |
| SODIUM OLEATE | 0.0001 |
| FOLIC ACID | 0.0001 |
| CALCIUM PANTOTHENATE | 0.0001 |
| | 100.0000 |

Example 8

Day Cream

| Formula (INCI/CTFA adopted names) | % w/w |
|---|---|
| WATER (AQUA) | 68.2676 |
| HYDROGENATED COCO-GLYCERIDES | 3.0000 |
| ETHYLHEXYL METHOXYCINNAMATE | 3.0000 |
| PETROLATUM | 2.7001 |
| TRIETHYLHEXANOIN | 2.5000 |
| ISOSTEARYL ISOSTEARATE | 2.5000 |
| CETEARYL ALCOHOL | 2.2400 |
| PPG-15 STEARYL ETHER | 1.5000 |
| PEG-30 STEARATE | 1.4000 |
| BUTYL METHOXYDIBENZOYLMETHANE | 1.4000 |
| STEARYL ALCOHOL | 1.2250 |
| MYRISTYL ALCOHOL | 1.0750 |
| *OLEA EUROPAEA* (OLIVE) FRUIT OIL | 1.0000 |
| BEESWAX (CERA ALBA) | 1.0000 |
| PHENOXYETHANOL | 0.9376 |
| BUTYLENE GLYCOL | 0.5834 |
| CETEARETH-20 | 0.5600 |
| CETYL ALCOHOL | 0.5500 |
| TOCOPHERYL ACETATE | 0.5000 |
| CETEARETH-25 | 0.4250 |
| *CAMELLIA SINENSIS* LEAF EXTRACT | 0.3750 |
| CYCLOPENTASILOXANE | 0.3250 |
| METHYLPARABEN | 0.3127 |
| LANOLIN ALCOHOL | 0.3007 |
| ACRYLATES/C10-30 ALKYL ACRYLATE CROSSPOLYMER | 0.3000 |
| HEXYL CINNAMAL | 0.2016 |
| PROPYLPARABEN | 0.2008 |
| ETHYLPARABEN | 0.2002 |
| CETEARETH-15 | 0.1875 |
| CYCLOHEXASILOXANE | 0.1750 |
| EDTA | 0.1551 |
| SODIUM HYDROXIDE | 0.1258 |
| FRAGRANCE (PARFUM) | 0.1173 |
| SODIUM CITRATE | 0.1000 |
| ETHYLHEXYLGLYCERIN | 0.1000 |
| ETHYLHEXYL SALICYLATE | 0.1000 |
| LECITHIN | 0.0915 |
| BHT | 0.0500 |
| *ZEA MAYS* (CORN) KERNEL EXTRACT | 0.0450 |
| MYRETH-4 | 0.0375 |
| LINALOOL | 0.0235 |
| SOLUBLE COLLAGEN | 0.0171 |
| LIMONENE | 0.0101 |
| GLYCERIN | 0.0100 |
| ALCOHOL | 0.0100 |
| XANTHAN GUM | 0.0083 |
| CITRIC ACID | 0.0080 |
| TRIHYDROXYPALMITAMIDOHYDROXYPROPYL MYRISTYL ETHER | 0.0078 |
| ALPHA-ISOMETHYL IONONE | 0.0068 |
| CITRAL | 0.0061 |
| CHITOSAN | 0.0046 |
| HYDROXYISOHEXYL 3-CYCLOHEXENE CARBOXALDEHYDE | 0.0030 |
| SODIUM CHLORIDE | 0.0027 |
| BUTYLPHENYL METHYLPROPIONAL | 0.0024 |
| *GLYCINE SOJA* (SOYBEAN) OIL | 0.0020 |
| SODIUM CHONDROITIN SULFATE | 0.0019 |
| GLUCOSE | 0.0019 |
| BUTYLPARABEN | 0.0017 |
| BENZYL SALICYLATE | 0.0016 |
| HYDROGENATED LECITHIN | 0.0010 |
| LYSINE HCL | 0.0006 |
| OLIGOPEPTIDE-21 | 0.0005 |
| CITRONELLOL | 0.0005 |
| THREONINE | 0.0004 |
| ISOBUTYLPARABEN | 0.0004 |
| DISODIUM EDTA | 0.0004 |
| ARGININE | 0.0004 |
| SERINE | 0.0002 |

-continued

| Formula (INCI/CTFA adopted names) | % w/w |
|---|---|
| POTASSIUM CHLORIDE | 0.0002 |
| HISTIDINE | 0.0002 |
| GERANIOL | 0.0002 |
| TRYPTOPHAN | 0.0001 |
| SODIUM PHOSPHATE | 0.0001 |
| SODIUM OLEATE | 0.0001 |
| MAGNESIUM SULFATE | 0.0001 |
| GLYCINE | 0.0001 |
| CALCIUM CHLORIDE | 0.0001 |
| ISOEUGENOL | 0.0001 |
| HYDROXYCITRONELLAL | 0.0001 |
| FOLIC ACID | 0.0001 |
| CALCIUM PANTOTHENATE | 0.0001 |
| BENZYL ALCOHOL | 0.0001 |
|  | 100.0000 |

The following Examples describe comparative experiments which were carried out with (a) (i) a combination of collagen, chitosan and sodium condroitin sulfate (hereafter "MPC") and (ii) MPC plus oligopeptide-21 (hereafter "MPC+IDP4");

(b) (i) a composition comprising glycoproteins 1 and 2 and ginseng and horsetail extracts (hereafter "GPVE") and (ii) GPVE plus oligopeptide-21 (hereafter "GPVE+IDP4");

(c) (i) a combination of MPC and GPVE (hereafter "GPVE/MPC") and (ii) a combination of GPVE/MPC and oligopeptide-21 (hereafter "GPVE/MPC+IDP4").

MPC is commercially available as Molecular Patch Complex from Coletica, Lyon, France. This product was filtered using a 0.22 μl filter and used as such. The concentrations thereof are in % w/w. IDP4 was employed as a solution of 500 mg of oligopeptide-21 in 1 L of water. "STDEV" means Standard Deviation.

Example 9

Cell Growth Assay

The effect of the addition of MPC vs. (MPC+IDP4), GPVE vs. (GPVE+IDP4), and GPVE/MPC vs. (GPVE/MPC=IDP4) on the growth of the following cells was investigated:
1. HacaT keratinocyte cell line
2. NIH3T3 fibroblast cell line
3. MSC (mesenchymal stem cells).
   Method:
(1) Cell seeding
(2) Starvation for 24 h with serum-free DMEM media
(3) Sample treatment
(4) Cultivation for 72 h
(5) Cell harvesting
(6) Cell growth assay The obtained results are summarized in the tables below:

|  | control | 0.02% | 0.20% | 2% | 0.02% | 0.20% | 2% |
|---|---|---|---|---|---|---|---|
|  |  | MPC | | | MPC + IDP4 | | |
| HacaT | 100 | 104 | 108 | 148 | 100 | 118 | 153 |
| STDEV | 2.942 | 10.345 | 4.689 | 5.33 | 8.036 | 4.995 | 9.365 |
| NIH3T3 | 100 | 119 | 123 | 134 | 205 | 202 | 200 |
| STDEV | 10.23 | 15.24 | 10.235 | 6.965 | 15.234 | 5.6987 | 10.662 |
| MSC | 100 | 102 | 107 | 117 | 120 | 121 | 130 |
| STDEV | 10.124 | 4.085 | 7.023 | 10.012 | 8.365 | 4.251 | 7.953 |
|  |  | GPVE | | | GPVE + IDP4 | | |
| HacaT | 100 | 120 | 147 | 199 | 137 | 156 | 185 |
| STDEV | 5 | 9.435 | 15.224 | 10.054 | 4.253 | 8.032 | 9.102 |
| NIH3T3 | 100 | 110 | 171 | 272 | 165 | 183 | 323 |
| STDEV | 2.502 | 4.921 | 10.234 | 5.241 | 7.653 | 4.932 | 10.495 |
| MSC | 100 | 104 | 337 | 117 | 98 | 337 | 335 |
| STDEV | 3.958 | 6.324 | 5.216 | 10.523 | 5.236 | 4.662 | 6.321 |
|  |  | GPVE/MPC | | | GPVE/MPC + IDP4 | | |
| HacaT | 100 | 122 | 127 | 198 | 134 | 140 | 201 |
| STDEV | 5.112 | 5.995 | 5.022 | 2.001 | 4.953 | 2.123 | 8.798 |
| NIH3T3 | 100 | 126 | 158 | 356 | 171 | 222 | 406 |
| STDEV | 4.568 | 5.003 | 4.603 | 4.596 | 5.5452 | 5.33 | 3.986 |
| MSC | 100 | 110 | 123 | 165 | 130 | 142 | 180 |
| STDEV | 2.335 | 5.021 | 5.632 | 9.565 | 9.996 | 4.968 | 7.663 |

Additionally, the effect of the addition of IDP4, GPVE, MPC, GPVE/MPC, GPVE/MPC+IDPE and several other substances (THE TPS, Cbglyc and MEYM7) on the growth of keratinocytes, fibroblasts and mesenchymal stem cells was compared. The results are set forth in the following table.

|  | Haca T (%) | NIH3T3 (%) | MSC (%) |
|---|---|---|---|
| control | 100 | 100 | 100 |
| IDP4 10 μg/ml | 148 | 260 | 145 |
| GPVE 2% | 159 | 272 | 117 |
| MPC 2% | 148 | 134 | 117 |
| GPVE/MPC 2% | 198 | 356 | 165 |
| GPVE/MPC + IDP4 | 201 | 406 | 180 |
| THE 2% | 41 | 56 | 88 |
| TPS 2% | 59 | 91 | 117 |
| Cbglyc 2% | 85 | 110 | 79 |
| MEYM7 2% | 59 | 119 | 103 |

Figure 3:
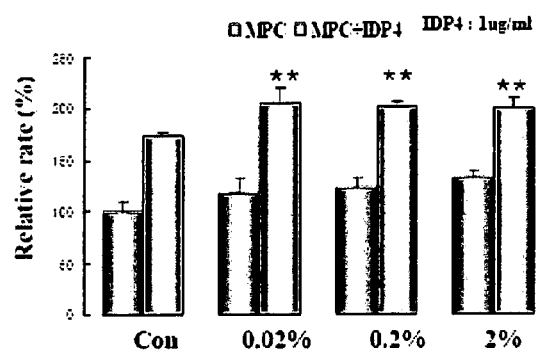
Figure 10:
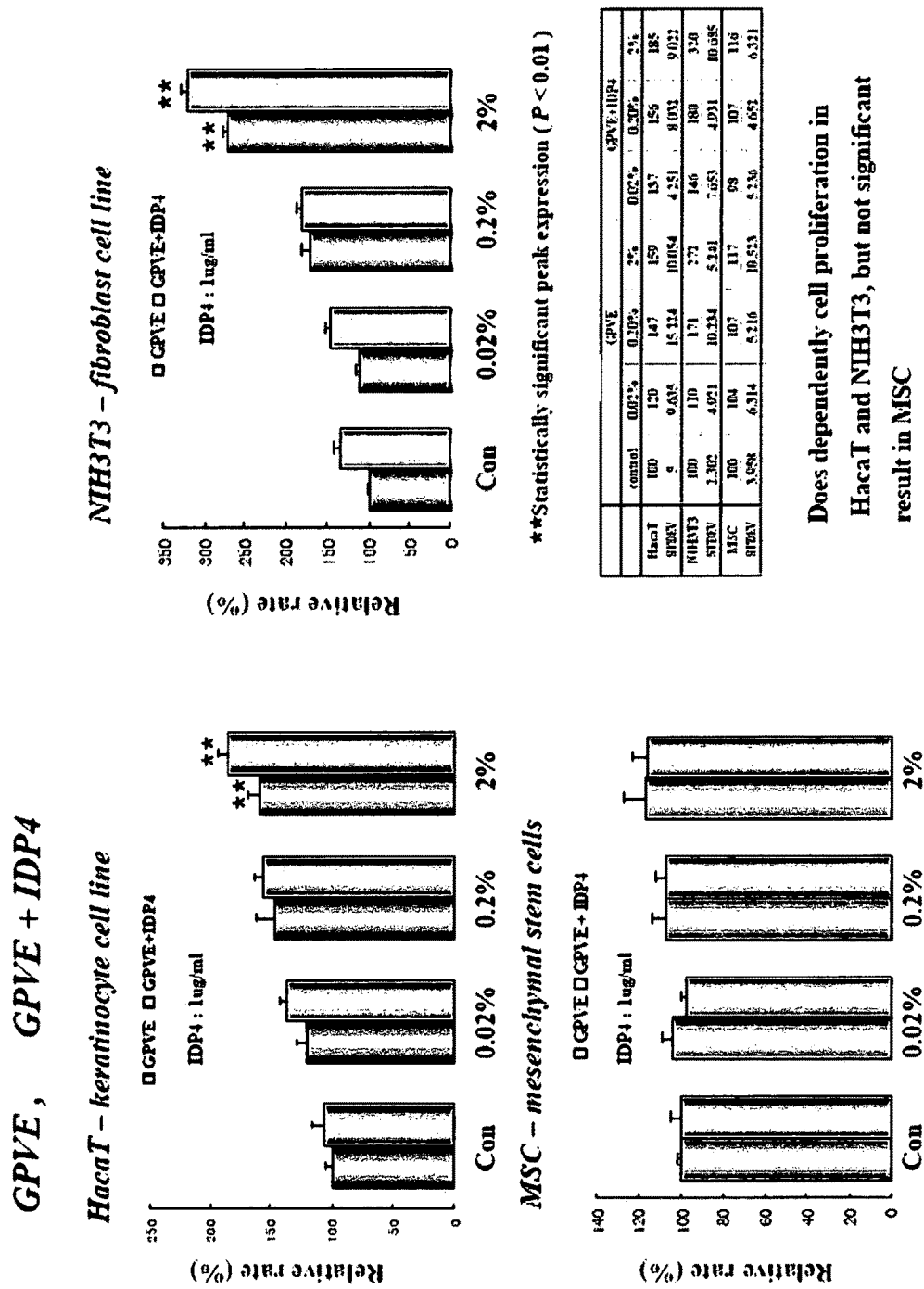

The data summarized in the above tables (and graphically represented in FIGS. 1-3, 10 and 11 wherein Con=Control) shows that in the case of MPC a statistically significant increase in cell growth was obtained with the keratinocyte cell line at a concentration of 2% MPC, both alone (FIG. 1, left bar) and in combination with IDP4 (FIG. 1, right bar), and that with the fibroblast cell line a statistically significant increase in cell growth was obtained at a concentration of as low as 0.02% MPC, but only in combination with IDP4 (FIG. 3). In the case of GPVE (FIG. 10) a statistically significant increase in cell growth was obtained with the keratinocyte cell line and the fibroblast cell line at a concentration of 2%, both with and without addition of IDP4. In the case of GPVE/MPC (FIG. 11) a statistically significant increase in cell growth was obtained with the keratinocyte cell line, the fibroblast cell line and the mesenchymal stem cells at a concentration of 2%, both with and without addition of IDP4. The addition of IPD4 alone at the concentration employed (1 µg) did not afford any statistically significant increase in growth with any of the tested cells.

Figure 12:
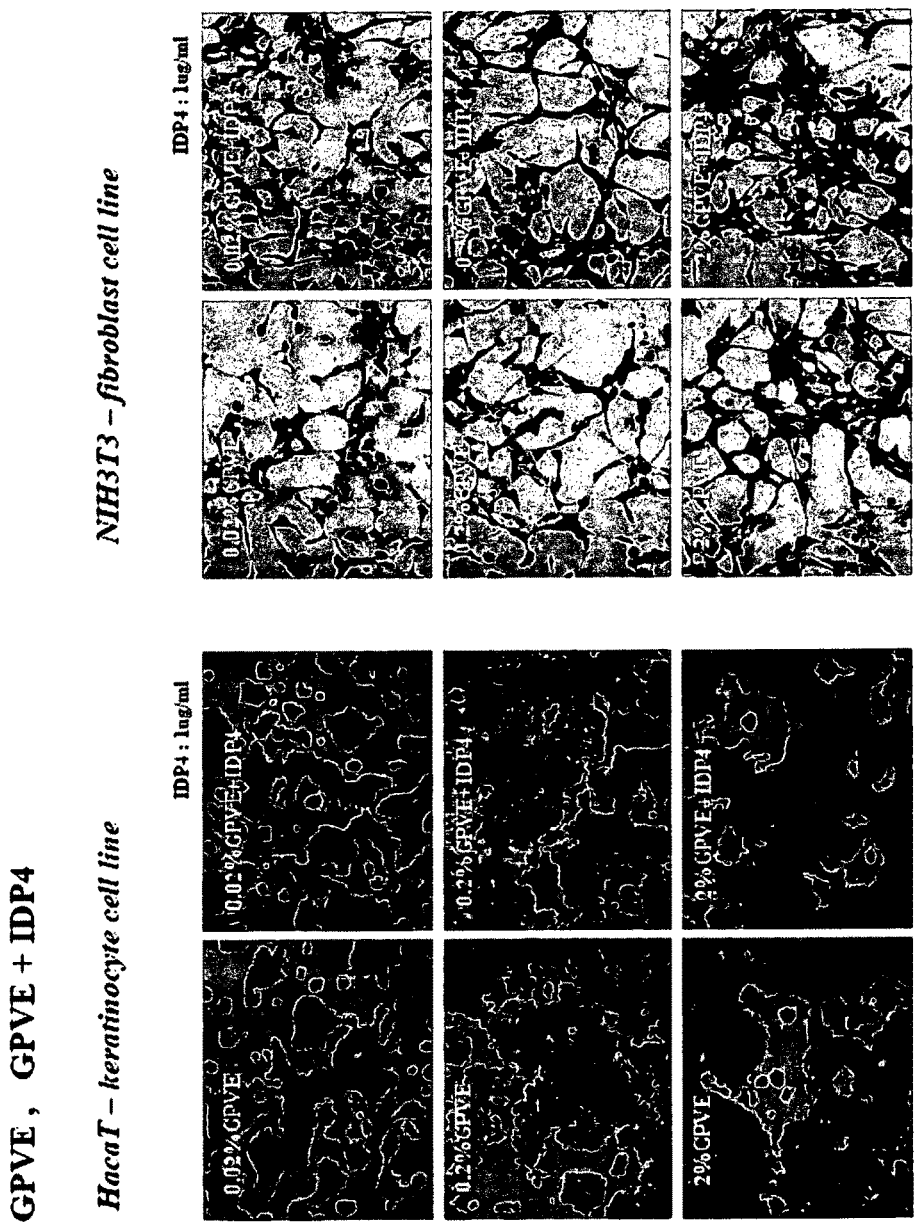
FIGS. 12-14 are photographs which illustrate the effect of the addition of GPVE and GPVE/MPC with or without IDP4 on keratinocytes, fibroblasts and mesenchymal stem cells.
Figure 13:
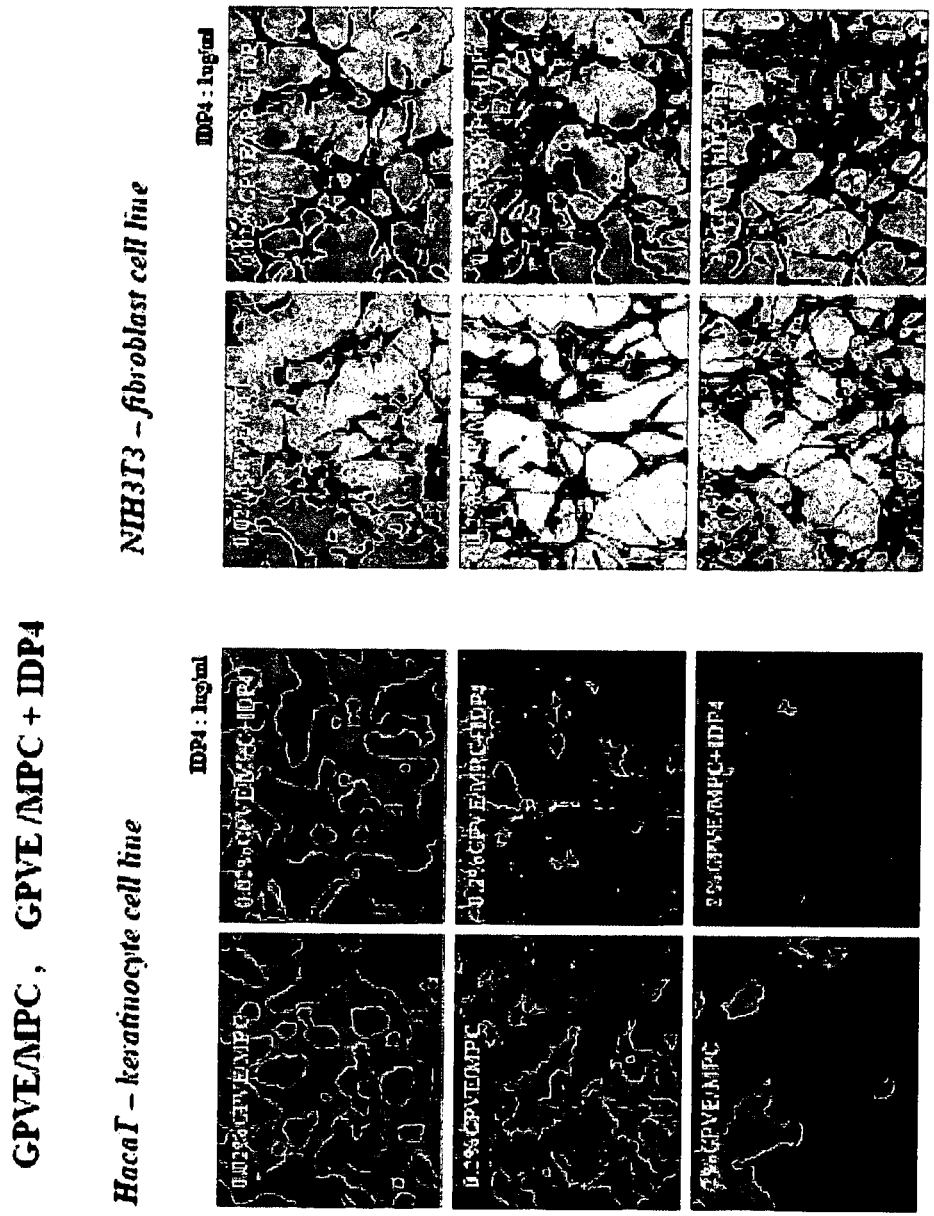
Figure 14:
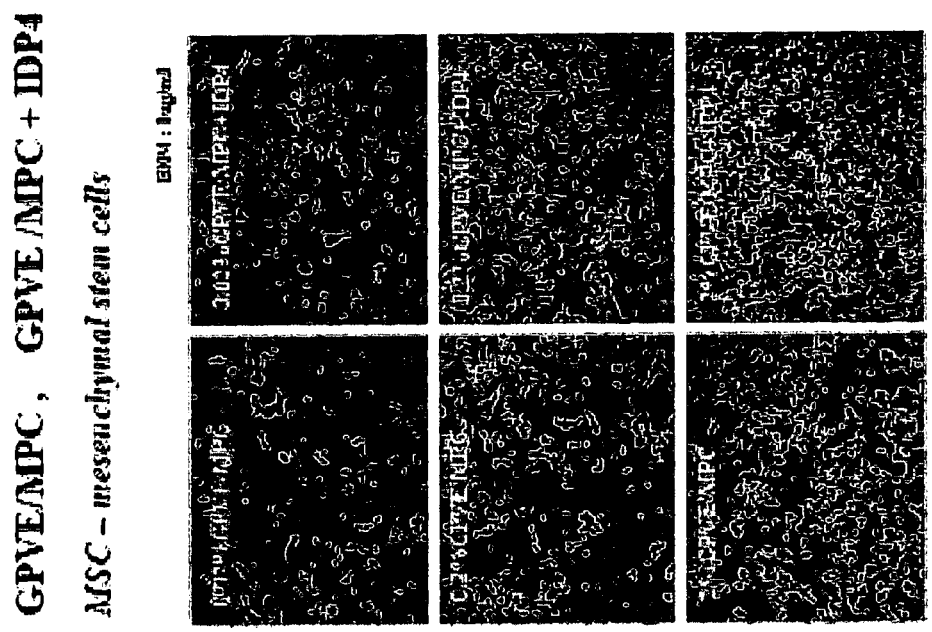

FIGS. 12-14 are photographs which illustrate the effect of the addition of GPVE and GPVE/MPC with or without IDP4 on the above cell lines.

Example 10

Extra Cellular Matrix (ECM) Expression

The effect of the addition of MPC and MPC+IDP4 on the extracellular matrix expression of procollagen, fibronectin, elastin, hyaluronic acid and laminine by the following cells was investigated:
1. HacaT keratinocyte cell line (hyaluronic acid, laminine)
2. NIH3T3 fibroblast cell line (procollagen, fibronectin, elastin).

Figure 4A:
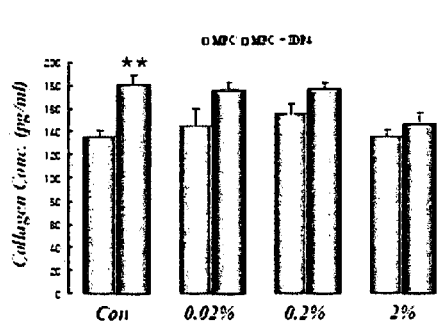
Figure 4B:
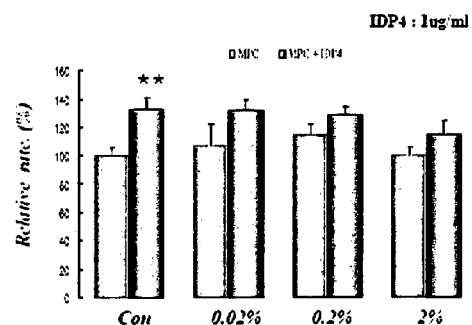

Method:
(1) Cell seeding
(2) Starvation for 24 h with serum-free DMEM media
(3) Sample treatment
(4) Cultivation for 72 h
(5) Cell supernatant collection
(6) Assay Assay (ELISA):
(a) Coating with capture antibody
(b) Blocking (blocking solution)
(c) Aspiration and washing each well five times
(d) Addition of sample and standard to each well
(e) Aspiration and washing each well five times
(f) Addition of conjugate to each well
(g) Aspiration and washing each well five times
(h) Addition of substrate solution to each well
(i) Addition of stop solution to each well
(j) Reading of optical density at 450 nm The obtained results are summarized in the tables below:

(a) Procollagen expression by fibroblast cells (see also FIGS. 4a and 4b; Con=Control):

|  |  | Collagen concentration (pg/ml) | | Relative rate (%) | |
|---|---|---|---|---|---|
|  | control | MPC 136 | MPC + IDP4 181 | MPC 100 | MPC + IDP4 133.1 |
| MPC | 0.02% | 227 | 272 | 166.9 | 200.0 |
|  | 0.20% | 272 | 280 | 200.0 | 205.9 |
|  | 2% | 136 | 227 | 100.0 | 166.9 |

Figure 5A:
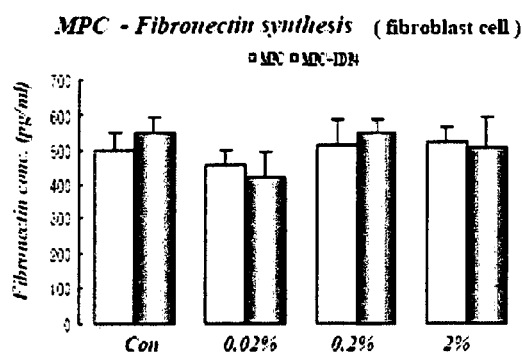
Figure 5B:
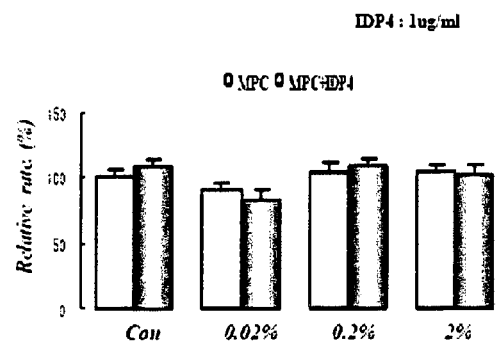

(b) Fibronectin expression by fibroblast cells (see also FIGS. 5a and 5b; Con=Control):

|  |  | MPC | MPC + IDP4 | MPC | MPC + IDP4 |
|---|---|---|---|---|---|
|  |  | fibronectin (pg/ml) | | Relative rate (%) | |
|  | control | 500 | 549 | 100 | 110 |
| MPC | 0.02% | 457 | 419 | 91 | 84 |
|  | 0.20% | 515 | 547 | 103 | 109 |
|  | 2% | 516 | 504 | 103 | 101 |

Figure 6A:
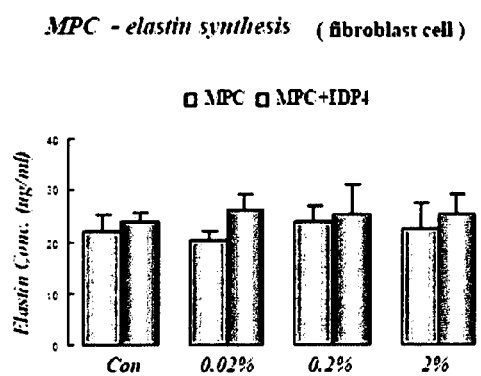
Figure 6B:
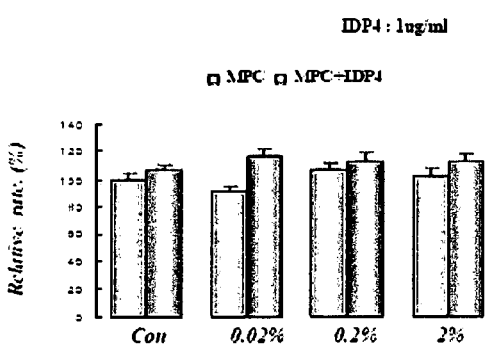

(c) Elastin expression by fibroblast cells (see also FIGS. 6a and 6b; Con=Control):

|  |  | MPC | MPC + IDP4 | MPC | MPC + IDP4 |
|---|---|---|---|---|---|
|  |  | Elastin (µg/ml) | | Relative rate (%) | |
|  | control | 22.2 | 23.77 | 100.0 | 107.1 |
| MPC | 0.02% | 20.2 | 26 | 91.0 | 117.1 |
|  | 0.20% | 23.8 | 25 | 107.2 | 112.6 |
|  | 2% | 22.5 | 25 | 101.4 | 112.6 |

(d) Hyaluronic acid expression by keratinocyte cells (see also FIGS. 7a and 7b; Con=Control):

|  |  | MPC | MPC + IDP4 | MPC | MPC + IDP4 |
|---|---|---|---|---|---|
|  |  | Hyaluronic acid (ng/ml) | | Relative rate (%) | |
|  | control | 223.15 | 273.77 | 100.0 | 122.7 |
| MPC | 0.02% | 309.92 | 344.85 | 138.9 | 154.5 |
|  | 0.20% | 383.68 | 500 | 171.9 | 224.1 |
|  | 2% | 515.63 | 703.13 | 231.1 | 315.1 |

(e) Laminine expression by keratinocyte cells (see also FIGS. 8a and 8b; Con=Control):

|  |  | MPC | MPC + IDP4 | MPC | MPC + IDP4 |
|---|---|---|---|---|---|
|  |  | Laminine (µg/ml) | | Relative rate (%) | |
|  | control | 23.15 | 33.77 | 100.0 | 145.9 |
| MPC | 0.02% | 39.2 | 34 | 169.3 | 146.9 |
|  | 0.20% | 33.68 | 40 | 145.5 | 172.8 |
|  | 2% | 35.63 | 43.13 | 153.9 | 186.3 |

The data summarized in the above tables shows that a statistically significant increase in the expression of hyaluronic acid was obtained with keratinocytes at a concentration of 2% MPC in combination with IDP4 (right bar). A statistically significant increase in the expression of hyaluronic acid was obtained neither with MPC alone nor with IDP4 alone.

Example 11

Protective Effect Against $H_2O_2$ (Anti-apoptosis Effect)

The protective (anti-apoptosis) effect of the addition of MPC and MPC+IDP4 on mesenchymal stem cells against $H_2O_2$ (free radical former) was tested.

Method:
(1) Cell seeding
(2) Starvation for 24 h with serum-free DMEM media
(3) Sample treatment
(4) Cultivation for 24 h
(5) Treatment with 5 mM $H_2O_2$
(6) Incubation for 24 h
(7) Cell growth assay The obtained results are summarized in the table below:

| | | W/O H₂O₂ | | | | |
|---|---|---|---|---|---|---|
| | control | IDP4 | 0% | 0.02% | 0.20% | 2% |
| | | | With H₂O₂ MPC | | | |
| MSC | 139 | 175 | 100 | 97 | 121 | 147 |
| | | | With H₂O₂ MPC + IDP4 | | | |
| | | | 110 | 105 | 148 | 170 |

Figure 9:
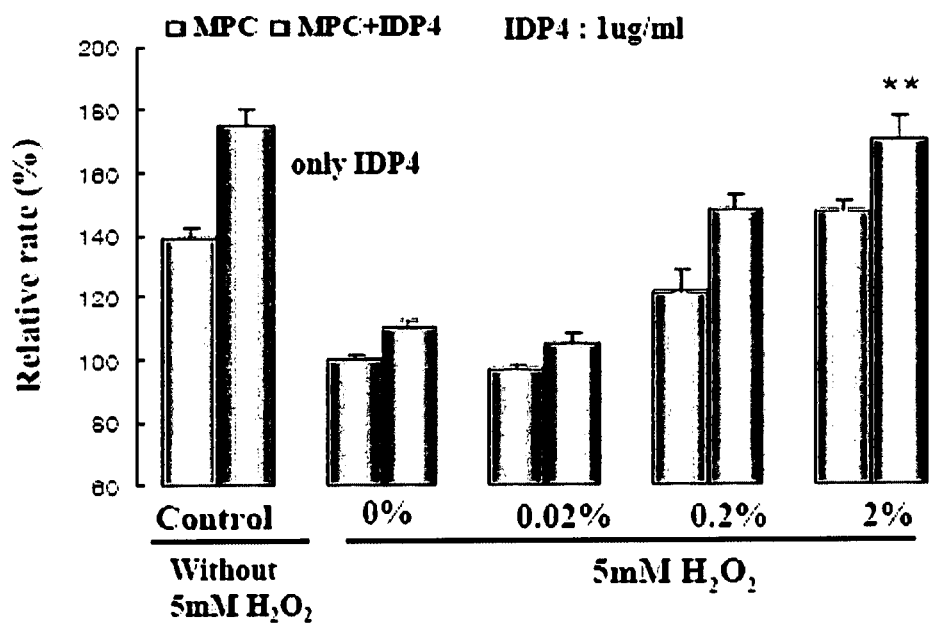
FIG. 9 is a graphic representation of the results obtained with mesenchymal stem cells in the anti-aptoptosis experiments described in Example 11 below.

The data summarized in the above table (and graphically represented in FIG. 9) shows that a statistically significant decrease in cell apoptosis and increase in cell prolifertion was obtained with the mesenchymal stem cells upon addition of 2% MPC, but only in combination with IDP4 (right bar).

Example 12

Extra Cellular Matrix (ECM) Expression

The effect of the addition of GPVE and GPVE+IDP4 on the extracellular matrix expression of procollagen, fibronectin, elastin, hyaluronic acid and laminine by the following cells was investigated:
1. HacaT keratinocyte cell line (hyaluronic acid, laminine)
2. NIH3T3 fibroblast cell line (procollagen, fibronectin, elastin).

Method:
(1) Cell seeding
(2) Starvation for 24 h with serum-free DMEM media
(3) Sample treatment
(4) Cultivation for 72 h
(5) Cell supernatant collection
(6) Assay Assay (ELISA):
(a) Coating with capture antibody
(b) Blocking (blocking solution)
(c) Aspiration and washing each well five times
(d) Addition of sample and standard to each well
(e) Aspiration and washing each well five times
(f) Addition of conjugate to each well
(g) Aspiration and washing each well five times
(h) Addition of substrate solution to each well
(i) Addition of stop solution to each well
(j) Reading of optical density at 450 nm The obtained results are summarized in the tables below:

(a) Procollagen expression by fibroblast cells (see also FIG. 15; Con=Control):

| | | GPVE | GPVE + IDP4 | GPVE | GPVE + IDP4 |
|---|---|---|---|---|---|
| | | Collagen concentration (pg/ml) | | Relative rate (%) | |
| GPVE | control | 81 | 102 | 100.0 | 125.9 |
| | 0.02% | 127 | 127 | 156.8 | 156.8 |
| | 0.20% | 227 | 181 | 280.2 | 223.5 |
| | 2% | 230 | 318 | 284.0 | 392.6 |

(b) Fibronectin expression by fibroblast cells (see also FIG. 16; Con=Control):

| | | GPVE | GPVE + IDP4 | GPVE | GPVE + IDP4 |
|---|---|---|---|---|---|
| | | fibronectin (pg/ml) | | Relative rate (%) | |
| GPVE | control | 500 | 526 | 100 | 105 |
| | 0.02% | 626 | 716 | 125 | 143 |
| | 0.20% | 762 | 805 | 152 | 161 |
| | 2% | 1,250 | 1,317 | 250 | 263 |

Figure 17:
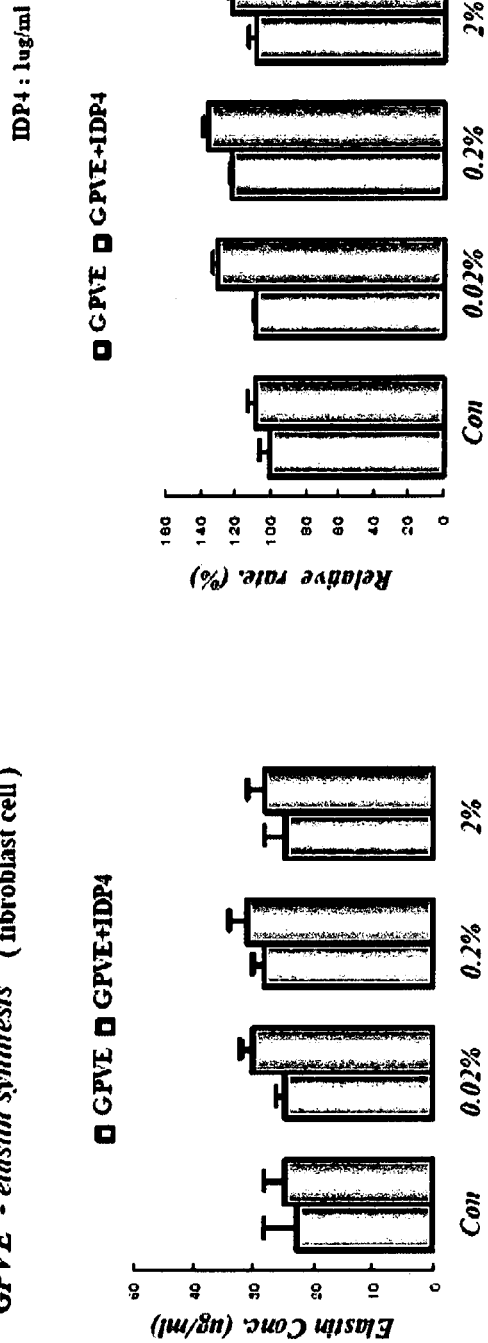

(c) Elastin expression by fibroblast cells (see also FIG. 17; Con=Control):

| | | GPVE | GPVE + IDP4 | GPVE | GPVE + IDP4 |
|---|---|---|---|---|---|
| | | Elastin (µg/ml) | | Relative rate (%) | |
| GPVE | control | 23 | 25 | 100.0 | 108.7 |
| | 0.02% | 25 | 30 | 108.7 | 130.4 |
| | 0.20% | 28 | 31 | 121.7 | 134.8 |
| | 2% | 25 | 28 | 108.7 | 121.7 |

Figure 18:
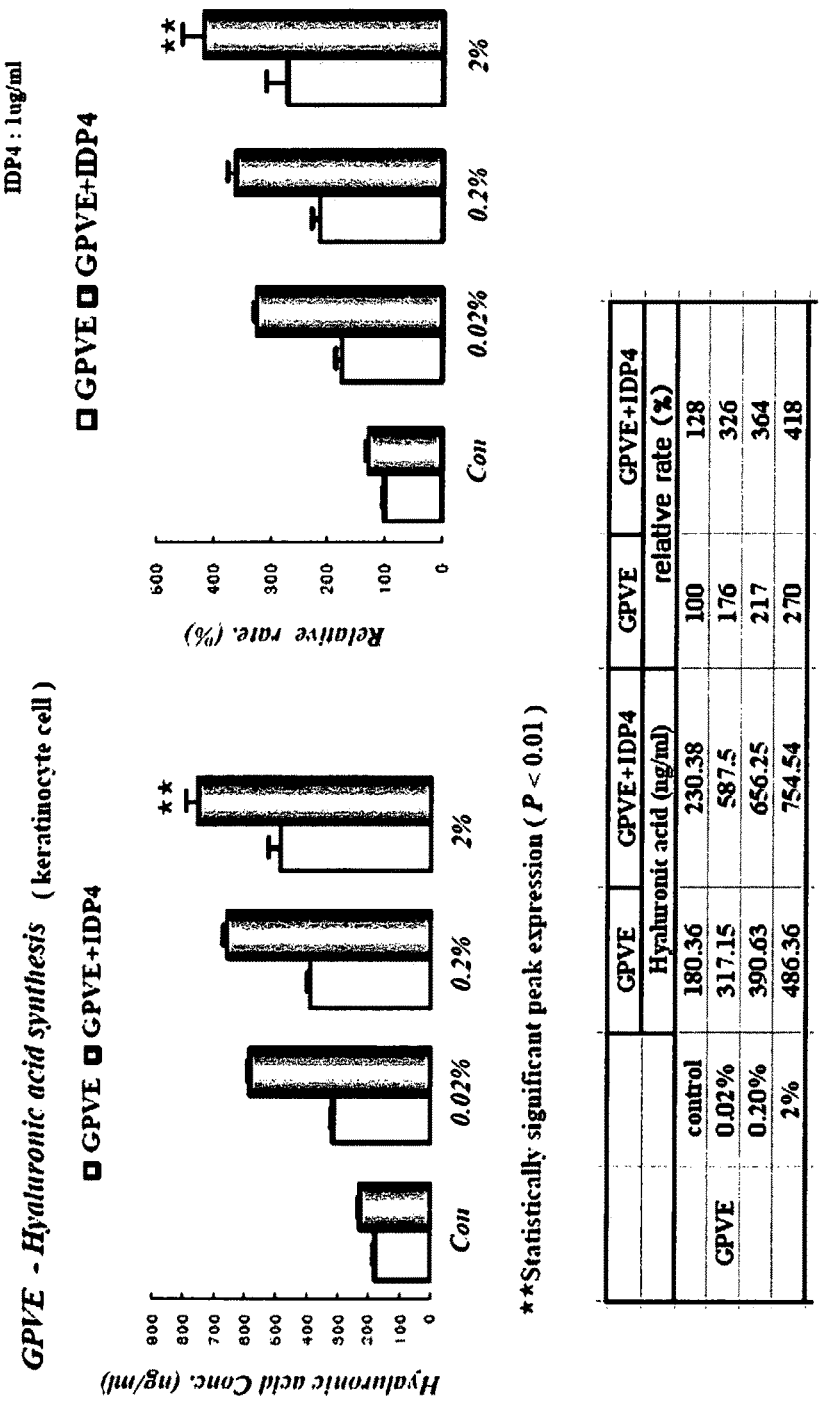

(d) Hyaluronic acid expression by keratinocyte cells (see also FIG. 18; Con=Control):

| | | GPVE | GPVE + IDP4 | GPVE | GPVE + IDP4 |
|---|---|---|---|---|---|
| | | Hyaluronic acid (ng/ml) | | Relative rate (%) | |
| GPVE | control | 180.36 | 230.38 | 100 | 128 |
| | 0.02% | 317.15 | 587.5 | 176 | 326 |
| | 0.20% | 390.63 | 656.25 | 217 | 364 |
| | 2% | 486.36 | 754.54 | 270 | 418 |

Figure 19:
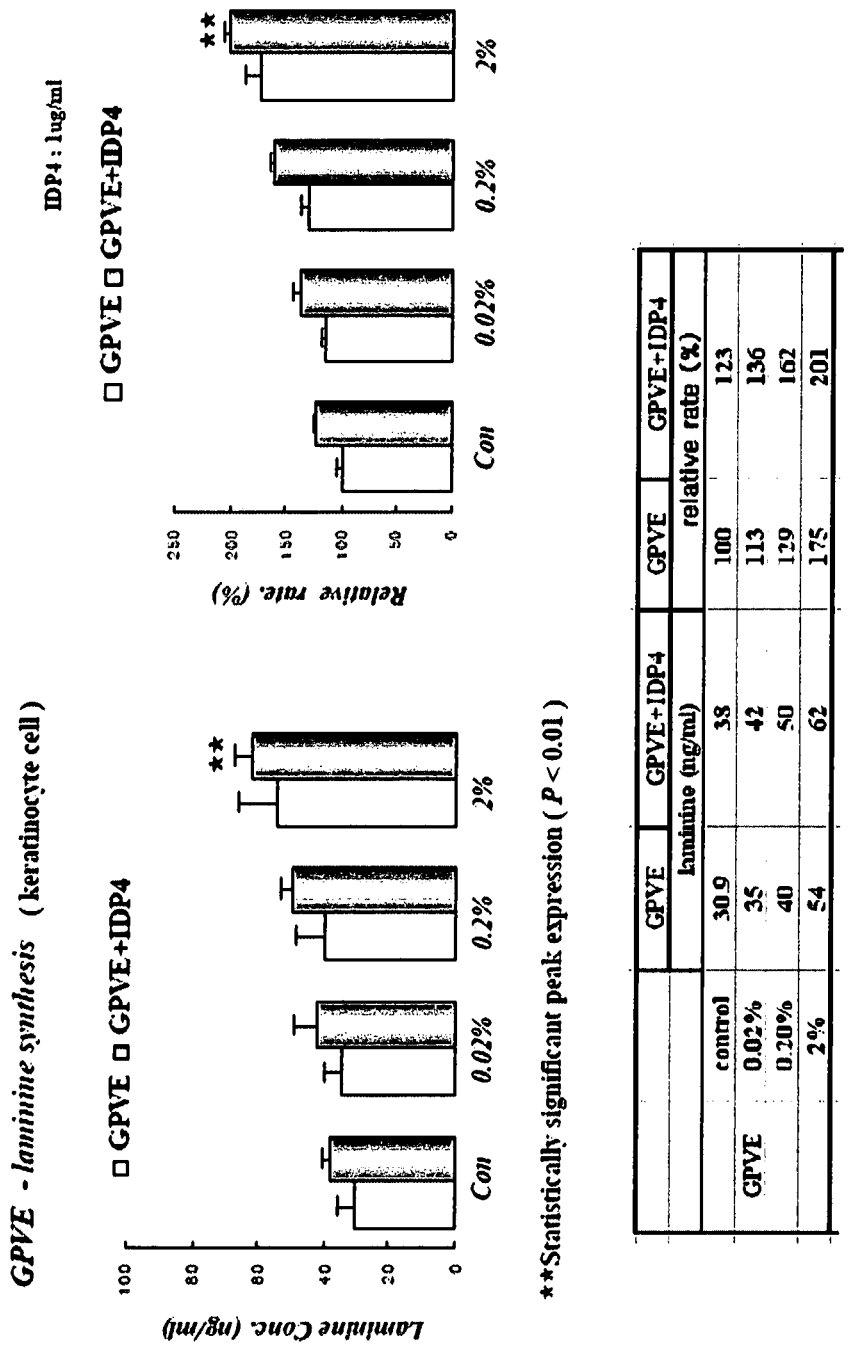

(e) Laminine expression by keratinocyte cells (see also FIG. 19; Con=Control):

| | | GPVE | GPVE + IDP4 | GPVE | GPVE + IDP4 |
|---|---|---|---|---|---|
| | | Laminine (µg/ml) | | Relative rate (%) | |
| GPVE | control | 30.9 | 38 | 100 | 123 |
| | 0.02% | 35 | 42 | 113 | 136 |
| | 0.20% | 40 | 50 | 129 | 162 |
| | 2% | 54 | 62 | 175 | 201 |

Figure 20:
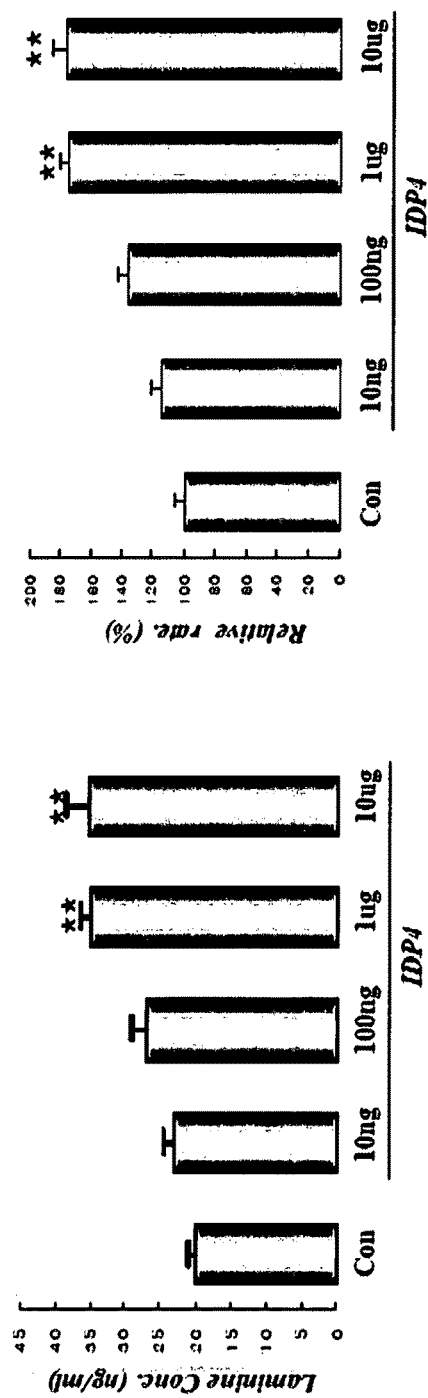
FIG. 20 is a graphic representation of the effect of the addition of different concentrations of IDP4 to keratinocytes on the expression of laminine.

The expression of procollagen, fibronectin, elastin, hyaluronic acid and laminine by keratinocyte cells and fibroblast cells as a function of the concentration of IDP4 was also investigated. The results are summarized in the table below (see also FIG. 20).

| | | procollagen % | fibronectin % | elastin % | hyaluronic acid % | laminine % |
|---|---|---|---|---|---|---|
| control | | 100 | 100 | 100 | 100 | 100 |
| IDP4 | 10 ng/ml | 175 | 101 | 131 | 110 | 115 |
| | 100 ng/ml | 226 | 105 | 127 | 137.5 | 135 |
| | 1 µg/ml | 302 | 116 | 137 | 150 | 175 |
| | 10 µg/ml | 333 | 158 | 131 | 160 | 177.5 |

The data summarized in the above tables shows a maximum increase of collagen expression when 2% of GPVE are added to fibroblast cells, and shows a dramatic increase of collagen expression when IDP4 is additionally added. The data also shows an increase in fibronectin expression at 2% GPVE plus IDP4. It also shows a stronger increase in hyaluronic acid and laminine expression when 2% GPVE and additionally IDP4 are present.

Example 13

Extra Cellular Matrix (ECM) Expression

The effect of GPVE/MPC and GPVE/MPC+IDP4 on the extracellular matrix expression of procollagen, fibronectin, elastin, hyaluronic acid and laminine by the following cells was investigated:
1. HacaT keratinocyte cell line (hyaluronic acid, laminine)
2. NIH3T3 fibroblast cell line (procollagen, fibronectin, elastin).

Figure 21:
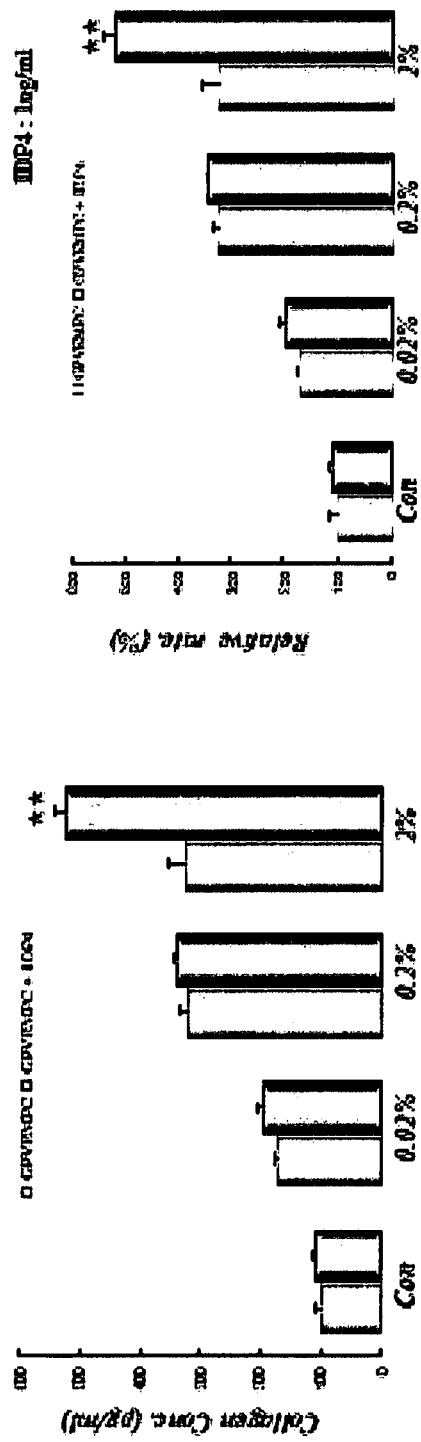

Method:
(1) Cell seeding
(2) Starvation for 24 h with serum-free DMEM media
(3) Sample treatment
(4) Cultivation for 72 h
(5) Cell supernatant collection
(6) Assay Assay (ELISA):
(a) Coating with capture antibody
(b) Blocking (blocking solution)
(c) Aspiration and washing each well five times
(d) Addition of sample and standard to each well
(e) Aspiration and washing each well five times
(f) Addition of conjugate to each well
(g) Aspiration and washing each well five times
(h) Addition of substrate solution to each well
(i) Addition of stop solution to each well
(j) Reading of optical density at 450 nm The obtained results are summarized in the tables below:

(a) Procollagen expression by fibroblast cells (see also FIG. 21; Con=Control):

|  |  | GPVE/ MPC | GPVE/ MPC + IDP4 | GPVE/ MPC | GPVE/ MPC + IDP4 |
|---|---|---|---|---|---|
|  |  | Collagen concentration (pg/ml) | | Relative rate (%) | |
|  | control | 79 | 82 | 100 | 100 |
| GPVE/ MPC | 0.02% | 130 | 150 | 171 | 197 |
|  | 0.20% | 243 | 260 | 319 | 342 |
|  | 2% | 246 | 348 | 323 | 523 |

(b) Fibronectin expression by fibroblast cells (see also FIG. 22; Con=Control):

|  |  | GPVE/ MPC | GPVE/ MPC + IDP4 | GPVE/ MPC | GPVE/ MPC + IDP4 |
|---|---|---|---|---|---|
|  |  | fibronectin (pg/ml) | | Relative rate (%) | |
|  | control | 600 | 604 | 100 | 101 |
| GPVE/ MPC | 500 ng/ml | 600 | 632 | 100 | 105 |
|  | 5 μg/ml | 626 | 674 | 104 | 112 |
|  | 50 μg/ml | 1,508 | 1,843 | 251 | 307 |

Figure 23:
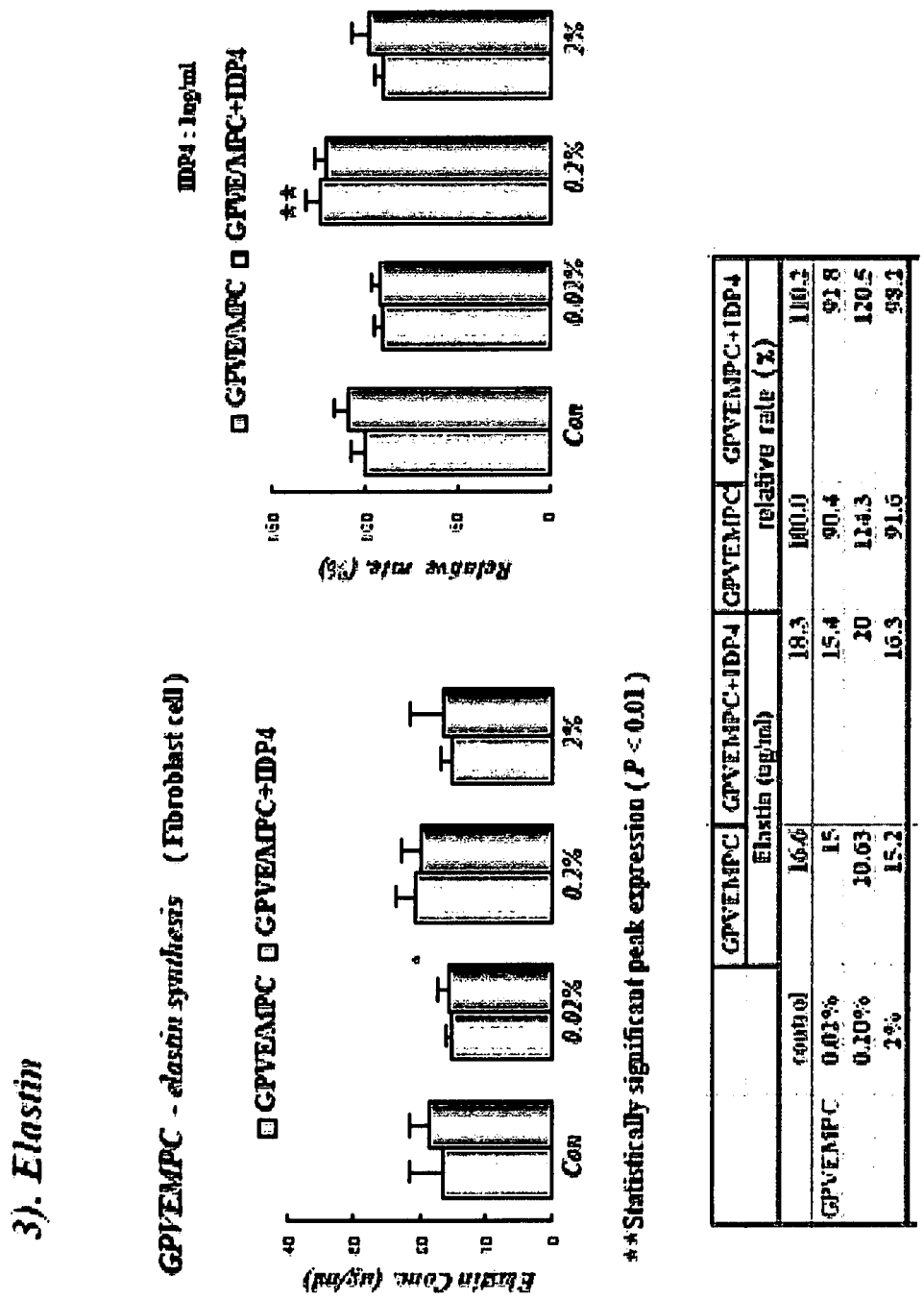

(c) Elastin expression by fibroblast cells (see also FIG. 23; Con=Control):

|  |  | GPVE/ MPC | GPVE/ MPC + IDP4 | GPVE/ MPC | GPVE/ MPC + IDP4 |
|---|---|---|---|---|---|
|  |  | Elastin (μg/ml) | | Relative rate (%) | |
|  | control | 16.6 | 18.3 | 100.0 | 110.2 |
| GPVE/ MPC | 0.02% | 15 | 15.4 | 90.4 | 92.8 |
|  | 0.20% | 20.63 | 20 | 124.3 | 120.5 |
|  | 2% | 15.2 | 16.3 | 91.6 | 98.2 |

Figure 24:
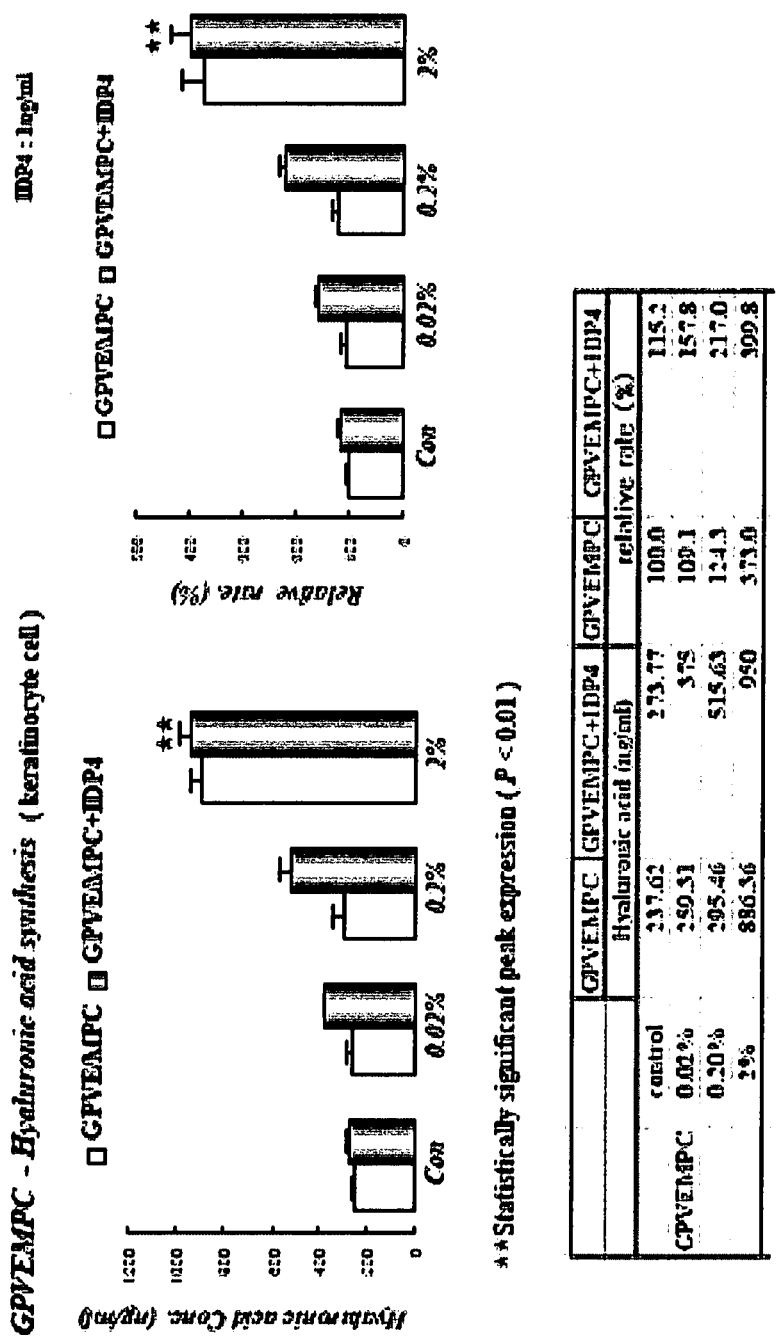

(d) Hyaluronic acid expression by keratinocyte cells (see also FIG. 24; Con=Control):

|  |  | GPVE/ MPC | GPVE/ MPC + IDP4 | GPVE/ MPC | GPVE/ MPC + IDP4 |
|---|---|---|---|---|---|
|  |  | Hyaluronic acid (ng/ml) | | Relative rate (%) | |
|  | control | 237.62 | 273.77 | 100.0 | 115.2 |
| GPVE/ MPC | 0.02% | 259.31 | 375 | 109.1 | 157.8 |
|  | 0.20% | 295.46 | 515.63 | 124.3 | 217.0 |
|  | 2% | 886.36 | 950 | 373.0 | 399.8 |

Figure 25:
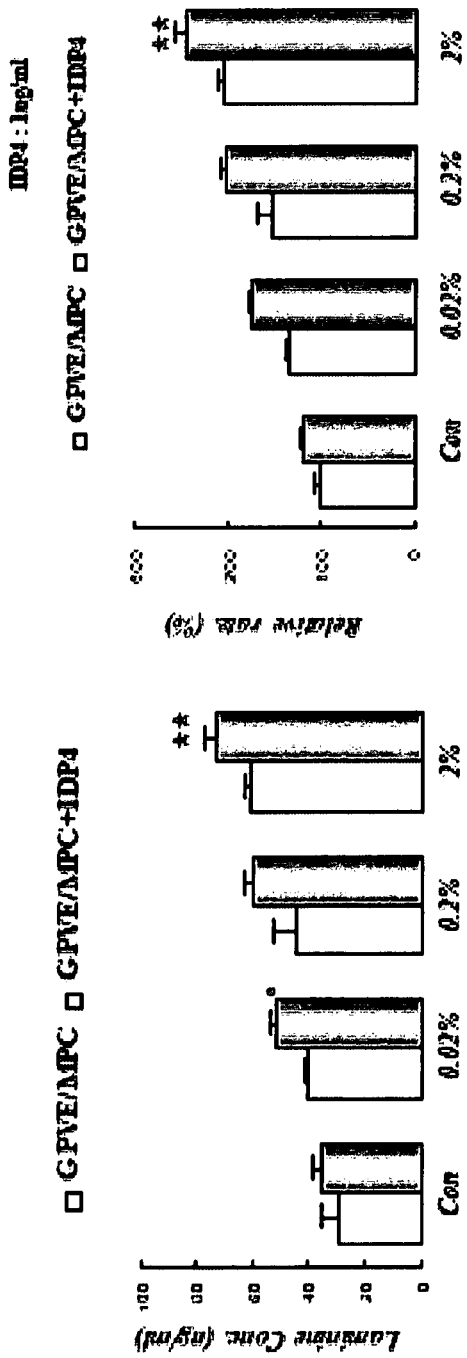

(e) Laminine expression by keratinbcyte cells (see also FIG. 25; Con=Control):

|  |  | GPVE/ MPC | GPVE/ MPC + IDP4 | GPVE/ MPC | GPVE/ MPC + IDP4 |
|---|---|---|---|---|---|
|  |  | Laminine (μg/ml) | | Relative rate (%) | |
|  | control | 29.7 | 35 | 100.0 | 117.8 |
| GPVE/ MPC | 0.02% | 40 | 52 | 134.7 | 175.1 |
|  | 0.20% | 45 | 60 | 151.5 | 202.0 |
|  | 2% | 61 | 73 | 205.4 | 245.8 |

The expression of procollagen, fibronectin, elastin, hyaluronic acid and laminine by keratinocyte cells and fibroblast cells in the presence of IDPE, GPVE, MPC, GPVE/MPC, GPVE/MPC+IDP4 as well as several other substances (THE, TPS, Chgly and MEYM7) was also compared. The results are summarized in the table below.

|  | procollagen % | fibronectin % | elastin % | hyaluronic acid % | laminine % |
|---|---|---|---|---|---|
| control | 100 | 100 | 100 | 100 | 100 |
| IDP4 10 μg/ml | 333 | 158 | 137 | 160 | 177.5 |
| GPVE 2% | 284 | 250 | 121 | 270 | 175 |
| MPC 2% | 166 | 103 | 107.2 | 231.1 | 169.3 |
| GPVE/MPC 2% | 323 | 251 | 124 | 373 | 205 |
| GPVE/MPC + IDP4 | 523 | 307 | 121 | 400 | 245 |
| THE 2% | 111 | 119 | 98 | 125 | 124 |
| TPS 2% | 118 | 119 | 125 | 137 | 93 |
| Chglyc 2% | 167 | 41 | 78 | 183 | 120 |
| MEYM7 2% | 165 | 87 | 81 | 63 | 65 |

The data summarized in the above tables shows a maximum increase of collagen expression of 140% when 2% of GPVE/MPC are added to fibroblast cells, and shows a dramatic increase of 350% collagen expression when IDP4 is additionally added. Substantially the same applies to fibronectin expression. The data also shows a maximum increase in hyaluronic acid and laminine expression when 2% GPVE and additionally IDP4 are added.

It is noted that the foregoing examples have been provided merely for the purpose of explanation and are in no way to be construed as limiting of the present invention.

While the present invention has been described with reference to an exemplary embodiment, it is understood that the words that have been used are words of description and illustration, rather than words of limitation. Changes may be made, within the purview of the appended claims, as presently stated and as amended, without departing from the scope and spirit of the present invention in its aspects. Although the invention has been described herein with reference to particular means, materials and embodiments, the invention is not intended to be limited to the particulars disclosed herein. Instead, the invention extends to all functionally equivalent structures, methods and uses, such as are within the scope of the appended claims.

What is claimed is:

1. A topical cosmetic or dermatological preparation for promoting skin cell growth and/or reducing or preventing scar tissue formation comprising effective amounts of:
    (a) collagen;
    (b) at least one of chitosan and an acetyl derivative thereof with a degree of acetylation of up to about 50%;
    (c) at least one glycosaminoglylcan; and
    (d) oligopeptide-21.

2. The preparation of claim 1, wherein the preparation further comprises
    (e) a composition comprising
        (i) glycoprotein 1;
        (ii) glycoprotein 2;
        (iii) ginseng extract; and
        (iv) horsetail extract.

3. The preparation of claim 1, wherein (d) is present in a form which prevents it from contacting (a), (b) and (c) directly.

4. The preparation of claim 1, wherein (d) is present in the form of a nanoemulsion.

5. The preparation of claim 1, wherein the preparation further comprises lecithin, glycerin and glycine soja oil.

6. The preparation of claim 1, wherein the preparation further comprises one or more skin cell culture media ingredients.

7. The preparation of claim 1, wherein the preparation comprises at least one of a nanosponge matrix and a microsponge matrix of substances (a) to (c), which nanosponge matrix or microsponge matrix comprises one or more cell culture media ingredients.

8. A cosmetic or dermatological product which comprises the preparation of claim 1 and is selected from an aqueous gel, an O/W emulsion, a W/O/W emulsion, a W/0 emulsion, and a microemulsion.

9. An article which comprises the preparation of claim 1 and is selected from a wound covering, a skin covering, a patch, a pad, a tissue and a bandage.

10. A polyurethane matrix which comprises incorporated therein the preparation of claim 1.

11. The preparation of claim 1, wherein a total concentration of components (a) to (c) is from about 0.005% to about 10% by weight, and (d) is present in a concentration of from about 0.0001% to about 1% by weight, each based on a total weight of the preparation.

12. The preparation of claim 11, wherein a total concentration of components (a) to (c) is from about 0.01% to about 1% by weight.

13. The preparation of claim 1, wherein the preparation comprises at least 30% by weight of water, based on a total weight of the preparation.

14. The preparation of claim 11, wherein the preparation comprises at least 50% by weight of water, based on a total weight of the preparation.

15. A topical cosmetic or dermatological preparation for promoting skin cell growth and/or reducing or preventing scar tissue formation comprising effective amounts of:
    (A) oligopeptide-21;
    (B) glycoprotein 1;
    (C) glycoprotein 2;
    (D) ginseng extract; and
    (E) horsetail extract.

16. The preparation of claim 15, wherein (A) is present in the form of a nanoemulsion.

17. The preparation of claim 15, wherein (A) is present in a concentration of from about 0.0001% to about 1% by weight, and (B), (C), (D), and (E) are present in a total concentration of from about 0.0001% to about 1% by weight, each based on a total weight of the preparation.

18. The preparation of claim 15, wherein the preparation comprises at least 30% by weight of water, based on a total weight of the preparation.

* * * * *